United States Patent [19]

Lawrence et al.

[11] Patent Number: 5,543,542

[45] Date of Patent: Aug. 6, 1996

[54] METHODS OF PREPARING α-PHOSPHONOSULFINATE SQUALENE SYNTHETASE INHIBITORS

[76] Inventors: R. Michael Lawrence, 48 W. Crown Ter., Yardley, Pa. 19067; Scott A. Biller, 136 Nancy La., Ewing, N.J. 08638; Olga M. Fryszman, 63 Riverside Dr., Princeton, N.J. 08540

[21] Appl. No.: 445,604

[22] Filed: May 22, 1995

Related U.S. Application Data

[62] Division of Ser. No. 295,121, Aug. 24, 1994, Pat. No. 5,447,922.

[51] Int. Cl.$^6$ .................................. C07F 9/38; C07F 9/40
[52] U.S. Cl. .......................... 558/87; 558/131; 558/177; 562/23
[58] Field of Search ........................ 558/87, 131; 562/23

[56] References Cited

U.S. PATENT DOCUMENTS

| | | |
|---|---|---|
| 2,965,665 | 12/1960 | Gaertner et al. . |
| 3,595,880 | 7/1971 | Firestone . |
| 3,657,282 | 4/1972 | Christensen et al. . |
| 4,032,521 | 6/1977 | Christensen et al. . |
| 4,254,215 | 3/1981 | Kramp et al. . |
| 4,696,693 | 9/1987 | Swerdloff et al. . |
| 4,795,815 | 1/1989 | Ternansky . |
| 5,011,938 | 4/1991 | Barnett et al. . |

FOREIGN PATENT DOCUMENTS

| | | |
|---|---|---|
| 890344980 | 12/1989 | European Pat. Off. . |
| 3739691A1 | 6/1989 | Germany . |
| WO8800061 | 1/1988 | WIPO . |
| WO9007513 | 7/1990 | WIPO . |
| WO9324495 | 12/1993 | WIPO . |

OTHER PUBLICATIONS

Burton, D. J., J. Am. Chem. Soc. 1989, 111, 1773–1776.
Su, D. et al, Can. J. Chem. 1989, 67, 1795–1799.
Farrington, G. K., et al, J. Med. Chem. 1985, 28, 1668–1673.
Musicki, B. et al, T.S. Tetrahedron Lett. 1991, 32, 1267–1270.
Carretero, J. C. et al, Tetrahedron 1987, 43, 5125–5134.
Callahan, L. et al, Analytical biochemistry 1989, 177, 67–71.
Amin, Dilip et al, "Bisphosphonates used for the treatment of bone disorders inhibit squalene sythase and cholesterol biosynthesis", Journal of Lipid Research, vol. 33, 1993, pp. 1657–1663.

*Primary Examiner*—Johann Richter
*Assistant Examiner*—Michael G. Ambrose
*Attorney, Agent, or Firm*—Burton Rodney

[57] ABSTRACT

α-Phosphonosulfinate compounds are provided which inhibit the enzyme squalene synthetase and thereby inhibit cholesterol biosynthesis. These compounds have the formula

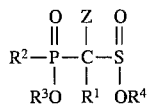

wherein $R^2$ is $OR^5$ or $R^{5a}$; $R^3$ and $R^5$ are independently H, alkyl, arylalkyl, aryl or cycloalkyl; $R^{5a}$ is alkyl, arylalkyl or aryl; $R^4$ is H or a pharmaceutically acceptable cation; Z is H, halogen, lower alkyl or lower alkenyl; and $R^1$ is a lipophilic group which contains at least 7 carbons and is alkyl, alkenyl, alkynyl, mixed alkenyl-alkynyl, aryl, arylalkyl, cycloalkyl, cycloalkylalkyl, heteroaryl, heteroarylalkyl, cycloheteroalkyl, cycloheteroalkylalkyl; including pharmaceutically acceptable salts.

9 Claims, No Drawings

METHODS OF PREPARING α-PHOSPHONOSULFINATE SQUALENE SYNTHETASE INHIBITORS

This is a division of application Ser. No. 295,121, filed Aug. 24, 1994, now U.S. Pat. No. 5,447,922.

FIELD OF THE INVENTION

The present invention relates to new α-phosphonosulfinate compounds which are useful in inhibiting cholesterol biosynthesis by inhibiting de novo squalene production, to hypocholesterolemic and antiatherosclerotic compositions containing such compounds and to a method of using such compounds for inhibiting cholesterol biosynthesis and atherosclerosis.

BACKGROUND OF THE INVENTION

Squalene synthetase is a microsomal enzyme which catalyzes the reductive dimerization of two molecules of farnesyl pyrophosphate (FPP) in the presence of nicotinamide adenine dinucleotide phosphate (reduced form) (NADPH) to form squalene (Poulter, C. D.; Rilling, H. C., in "Biosynthesis of Isoprenoid Compounds", Vol. I, Chapter 8, pp. 413–441, J. Wiley and Sons, 1981, and references therein). This enzyme is the first committed step of the de novo cholesterol biosynthetic pathway. The selective inhibition of this step should allow the essential pathways to isopentenyl tRNA, ubiquinone, and dolichol to proceed unimpeded. Squalene synthetase along with HMG-CoA reductase have been shown to be down-regulated by receptor mediated LDL uptake (Faust, J. R.; Goldstein, J. L.; Brown, M. S. *Proc. Nat. Acad Sci U.S.A.* 1979, 76, 5018–5022), lending credence to the proposal that inhibiting squalene synthetase will lead to an up-regulation of LDL receptor levels, as has been demonstrated for HMG-CoA reductase, and thus ultimately should be useful for the treatment and prevention of hypercholesterolemia and atherosclerosis.

U.S. Pat. No. 3,657,282 (Merck) (Division U.S. Pat. No. 3,822,296) discloses antibiotics of the structure

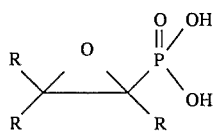

wherein R=SO$_3$H, SO$_2$R*, H, hydrocarbyl other than alkyl (eg. alkenyl, alkynyl, phenyl and naphthyl), substituted hydrocarbyl, CO$_2$H, CO$_2$R*, SO$_3$NR$_2$, heterocycle*, amino*, OH, OR, SH, SR, CHO, halogen, NO$_2$, CN, PO$_3$H$_2$, AsO$_3$H$_2$, acyl, —CHR$^1$R$^3$ where R$^1$=H, Me; R$^3$=R as above, preferably at least one R not=H, R preferably contains 1–10 carbons. *=optionally substituted.

Starting materials employed to prepare the above antibiotics include

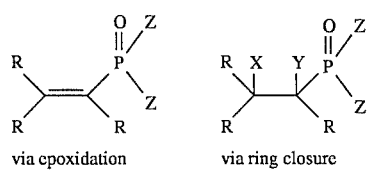

wherein R can be SO$_3$H, and X and Y are hydroxy or functional equivalent precursor to epoxide: eg. OH, halo, azide, RCO$_2$—, RSO$_2$O—, R$_2$S$^+$—, R$_3$N$^+$—, ArO—, R$_2$PO$_2$, RSO$_2$NR$^1$—. One of X and Y must be an oxygen radical.

EP 89/0-344-980 (Smith Kline) discloses α-antagonists of the structure

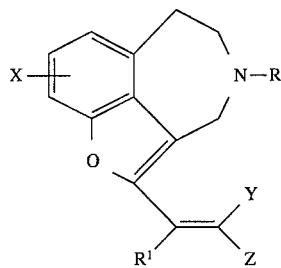

wherein Y or Z may be —SO$_2$R, —P(R)O(OR), —PR$_2$O, —PO(OR)$_2$, and amides.

WO 88/00061 (Amersham) discloses Technetium-99 complexes for Done scanning having the structure

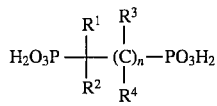

wherein R$^1$ and R$^3$=H, SO$_3$H or alkyl substituted with SO$_3$H and optionally one or more heteroatoms; R$^4$ can also be SO$_3$H or OH, NH$_2$, NHMe, NMe$_2$, lower alkyl substituted with a polar group; R$^2$=same as R$^4$ except not SO$_3$H and n=0, 1.

U.S. Pat. No. 4,032,521 (Merck) discloses intermediates, in cephalosporin synthesis, of the structures

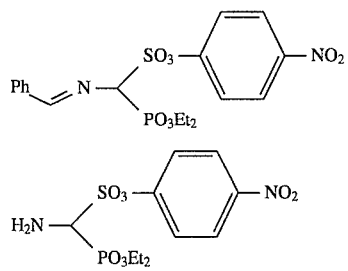

WO 90/07513 (Gas Research Institue) discloses electrolytes for fuel cells of the structure

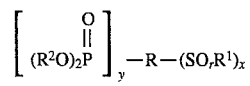

wherein
R=organic radicals with 1 or more F atoms;
R$^1$=H, alkali metal, Zn, Cd;
R$^2$=H, lower alkyl;
r=2, 3; and x, y=1, 2, 3.

U.S. Pat. No. 4,254,215 (Ciba Geigy AG) discloses a process for photographic developers wherein one component of a developer solution is:

wherein
n=1 to 4.
D=optionally substituted, saturated or unsaturated aliphatic radical (<40 carbons), can be interrupted by heteroatoms such as 0, SO$_2$, NH, NR.

$W=PO_3R_2$, $SO_3R$, $SO_2R$, $-NY-SO_3R$, $-SO_2NR_2$, $-SSO_3R$, $CO_2R$, $OH$, $NR_3^+$, $NR_2$, $CONR_2$.

DE 89/3739691-A (Hoechst) (Derwent #89-173507/24) discloses herbicides and plant growth regulators of the structure wherein Y=CH, N; X=O, S; Z=CH, N; $R^1$, $R^2$=C1–C6 alkyl or alkoxy; $R^3$=H, C1–C6 alkyl or alkoxy, C2–C6 alkenyl, alkynyl, alkenyloxy, alkynyloxy; all optionally substituted with one or more halogens; and $R^4$=H, C1–C4 alkyl or physiologically acceptable cation.

New intermediates are disclosed of the structures

Burton, D. J., J. Am. Chem. Soc. 1989, 111, 1773–1776 discloses electrolytes and chelators of the structures $(HO)_2P(O)CF_2SO_3Na$  $(HO)_2P(O)CF_2SO_3H$ Su, D.; Cen. W.; Kirchmeier, R. L.; Shreeve, J. M., Can. J. Chem. 1989, 67, 1795–1799, disclose electrolytes and chelators of the structures $(C_2H_5O)_2P(O)CFBrSO_3Na$  $(C_2H_5O)_2P(O)CFHSO_3Na$ $(HO)_2P(O)CFHSO_3Na$  $(HO)_2P(O)CFHSO_3H$ $(C_2H_5O)_2P(O)CF(SO_3Na)$  $(SO_2Na)$ $(C_2H_5O)_2P(O)CF(SO_3Na)_2$ Farrington, G. K.; Kumar, A.; Wedler, F. C., J. Med. Chem. 1985, 28, 1668–1673 discloses compound 10 as an inhibitor of aspartate transcarbamylase. Compound 24 is a synthetic intermediate.

Musicki, B.; Widlanski, T. S. Tetrahedron Lett. 1991, 32, 1267–1270 discloses compound 4 as a synthetic intermediate.

Carretero, J. C.; Demillequand, M.; Ghosez, L., Tetrahedron 1987, 43, 5125–5134 discloses $(EtO)_2P-CH_2SO_3X$ 1a X=Et
1b X=i-Pr
2a X=Li
2b X=n-Bu$_4$N for use in the synthesis of vinyl phosphonates via a Horner-Emmons reaction.

Callahan, L.; Ng, K.; Geller, D. H.; Agarwal, K.; Schwartz, N. B., Analytical Biochemistry 1989, 177, 67–71 discloses an analog of ADP (adenosine diphosphate) of the structure U.S. application Ser. No. 109,762 filed Aug. 20, 1993, discloses squalene synthetase inhibitors having the structure wherein $R^2$ is $OR^5$ or $R^{5a}$, $R^3$ and $R^5$ are independently H, alkyl, arylalkyl, aryl, cycloalkyl, metal ion or other pharmaceutically acceptable salt, or prodrug ester;

$R^{5a}$ is H, alkyl, arylalkyl or aryl;

$R^4$ is H, alkyl, aryl, cycloalkyl, arylalkyl, metal ion, or other pharmaceutically acceptable salt, or prodrug ester;

$R^1$ is a lipophitic group containing at least 7 carbons;

Z is H, halogen, lower alkyl or lower alkenyl.

The $R^1$ lipophilic group can be alkyl containing 7 to 25 carbons in the chain; alkenyl containing from 7 to 25 carbon atoms in the chain and from 1 to 6 double bonds; alkynyl containing 7 to 25 carbons in the chain and 1 to 6 triple bonds; mixed alkenyl-alkynyl containing 1 to 5 double bonds and 1 to 5 triple bonds; or aryl; and where in the above groups alkenyl, alkynyl and/or aryl may be substituted or unsubstituted; cycloheteroalkyl linked through a carbon on the ring or a heteroatom; cycloalkyl; heteroarylalkyl; cycloalkylalkyl; heteroaryl; cycloheteroalkylalkyl; or a group of the structure

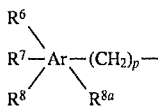

wherein Ar is aryl or heteroaryl, and Ar may include one to three additional rings fused to Ar, and wherein $(CH_2)_p$ contains from 1 to 15 carbons in the chain and may include 0, 1, 2 or 3 double bonds and/or 0, 1, 2 or 3 triple bonds in the normal chain, and may contain an ether or amino function in the chain, and/or may include 0, 1, 2 or 3 substituents as defined below for $R^6$; and $R^6$, $R^7$, $R^8$ and $R^{8a}$ are the same or different and are H, alkyl containing 1 to 40 carbons, alkoxy containing 1 to 40 carbons, alkenyl containing 2 to 40 carbons, alkenyloxy containing 2 to 40 carbons, alkynyl containing 2 to 40 carbons, alkynyloxy containing 2 to 40 carbons, hydroxy, halogen, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, heteroaryl, cycloalkyl, cycloatkylalkyl, Ar-alkyl, ArO, Ar-amino, Ar, Ar-thio, Ar-sulfinyl, Ar-sulfonyl, cyano, Ar-carbonyloxy, or Ar-carbonylamino.

DESCRIPTION OF THE INVENTION

In accordance with the present invention, there is provided α-phosphonosulfinate compounds which inhibit cholesterol biosynthesis, and thus are useful as hypocholesterolemic and antiatherosclerotic agents and have the following structure I.

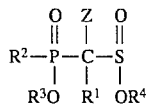

including pharmaceutically acceptable salts thereof and stereoisomers and enantiomers thereof;

wherein $R^2$ is $OR^5$ or $R^{5a}$;

$R^3$ and $R^5$ are the same or different and are H, alkyl, arylalkyl, aryl, cycloalkyl, a metal ion or other pharmaceutically acceptable cations or salts as defined below,;

$R^{5a}$ is alkyl, arylalkyl or aryl;

$R^4$ is H, metal ion or other pharmaceutically acceptable cations or salts as defined below;

Z is H, halogen, lower alkyl or lower alkenyl;

$R^1$ is a lipophilic group containing at least 7 carbons and is alkyl containing 7 to 25 carbons in the chain; alkenyl containing from 7 to 25 carbon atoms in the chain and from 1 to 6 double bonds; alkynyl containing 7 to 25 carbon atoms in the chain and from 1 to 6 triple bonds; mixed alkenyl-alkynyl containing 1 to 5 double bonds and 1 to 5 triple bonds;,aryl; cycloalkyl; cycloheteroalkyl linked through a carbon on the ring or a heteroatom; heteroaryl; heteroarylalkyl; cycloalkylalkyl; cycloheteroalkylalkyl; wherein any of the above groups may be optionally substituted; or $R^1$ is a group of the structure

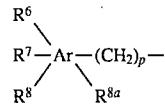

wherein Ar is aryl (such as phenyl or naphthyl), heteroaryl (5 or 6 membered) and may include one to three additional rings fused to Ar ( such as aryl, cycloalkyl, heteroaryl or cycloheteroalkyl) and wherein $(CH_2)_p$ contains from 1 to 15 carbons, preferably 2 to 12 carbons, in the chain and may include 0, 1, 2 or 3 double bonds and/or 0, 1, 2 or 3 triple bonds in the normal chain, and may contain an ether or amino function in the chain, and/or may include 0, 1, 2 or 3 substituents as defined below for $R^6$; and $R^6$, $R^7$, $R^8$ and $R^{8a}$ are the same or different and are H, alkyl containing 1 to 40 carbons, preferably from 3 to 25 carbons, alkoxy containing 1 to 40 carbons, preferably from 3 to 25 carbons, alkenyl containing 2 to 40 carbons, preferably from 3 to 25 carbons, alkenyloxy containing 2 to 40 carbons, preferably from 3 to 25 carbons, alkynyl containing 2 to 40 carbons, preferably from 3 to 25 carbons, alkynyloxy containing 2 to 40 carbons, preferably from 3 to 25 carbons, cycloheteroalkyl, cycloheteroalkylalkyl, heteroaryl, cycloalkyl, cycloalkylalkyl, Ar-alkyl, (such as arylalkyl), ArO (such as aryloxy), Ar-amino (such as arylaminoi, hydroxy, halogen, nitro, Ar (such as aryl), amino, substituted amino wherein the amino includes 1 or 2 substituents (which are alkyl, alkenyl, aryl or any of the Ar groups mentioned above), thiol, alkylthio, Ar-thio (such as arylthio), alkyl-sulfinyl, Ar-sulfinyl (such as arylsulfinyl), alkylsulfonyl, Ar-sulfonyl (such as arylsulfonyl), carboxy, cyano, alkoxycarbonyl, aminocarbonyl, alkylcarbonyloxy, Ar-carbonyloxy (such as arylcarbonyloxy), Ar-carbonylamino (such as arylcarbonylamino) or alkylcarbonylamino, as well as any of the Ar groups as defined above, and preferably wherein the total number of carbons in the substituted Ar-$(CH_2)_p$- group exceeds 10 carbons;

including pharmaceutically acceptable cations or salts thereof such as alkali metal salts such as lithium, sodium or potassium, alkaline earth metal salts such as calcium or magnesium, as well as zinc or aluminum and other FDA approved cations such as ammonium, choline, diethanolamine, ethylenediamine, and salts of naturally occuring amino acids such as arginine, lysine, alanine and the like.

The $(CH_2)_p$ group may contain 1, 2, 3 or more alkyl, alkoxy, alkenyl, alkynyl, hydroxy and/or halogen substituents as well as any of the substituents defined for $R^6$.

The compounds of formula I may also be depicted by the following structural formula:

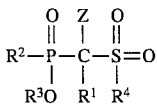

It will also be appreciated that in all cases herein, the moiety

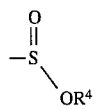

is equivalent to

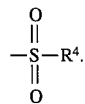

Thus, the compounds of the invention include the following sub-genuses:

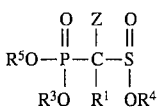  IA

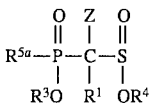  IB

In addition, in accordance with the present invention, new intermediates are provided having the structure

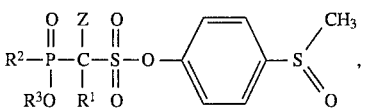  V

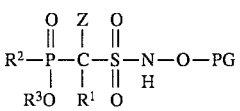  VI or

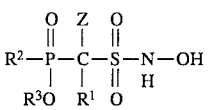  VII wherein $R^1$, $R^2$ and $R^3$ are as defined above and PG is a protecting group, with the proviso that $R^3$ and $R^5$ are alkyl, aryalkyl, aryl or cycloalkyl.

Unless otherwise indicated, the term "lower alkyl" or "alkyl" as employed herein alone or as part of another group includes both straight and branched chain hydrocarbons, containing 1 to 40 carbons, preferably 1 to 20 carbons, in the normal chain, more preferably 1 to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as F, Br, Cl or I or $CF_3$, alkoxy, aryl, arylalkyl, alkenyl, cycloalkyl, amino, hydroxy, alkylamido, alkanoylamino, arylcarbonylamino, nitro, cyano, thiol and/or alkylthio, as well as any of the other substituents as defined for $R^6$.

Unless otherwise indicated, the term "cycloalkyl" as employed herein alone or as part of another group includes saturated or partially unsaturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, cyclohexenyl, any of which groups may be substituted with 1 to 4 substituents such as halogen, alkyl, alkoxy, hydroxy, aryl, arylalkyl, cycloalkyl, alkylamido, alkanoylamino, arylcarbonylamino, amino, nitro, cyano, thiol and/or alkylthio, as well as any of the other substituents as defined for $R^6$.

Unless otherwise indicated, the term "aryl" as employed herein refers to monocyclic or bicyclic aromatic groups containing from 6 to 10 carbons in the ring portion, such as phenyl, naphthyl, or phenyl or naphthyl substituted with 1 to 4 substituents such as alkyl, halogen (Cl, Br or F), alkoxy, hydroxy, amino, alkanoylamino, arylcarbonylamino, aryl, arylalkyl, cycloalkyl, alkylamido, nitro, cyano, thiol and/or alkylthio, as well as any of the other substituents as defined for $R^6$.

The term "aralkyl", "aryl-alkyl" or "aryl-lower alkyl" as used herein alone or as part of another group refers to alkyl groups as discussed above having an aryl substituent, such as benzyl or phenethyl, or naphthylpropyl.

The term "lower alkoxy", "alkoxy", "aryloxy" or "aralkoxy" as employed herein alone or as part of another group includes any of the above alkyl, aralkyl or aryl groups linked to an oxygen atom.

The term "lower alkylthio", "alkylthio", "arylthio" or "aralkylthio" as employed herein alone or as part of another group includes any of the above alkyl, alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 40 carbons, preferably 3 to 30 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, alkyl, alkoxy, alkenyl, alkynyl, aryl, arylalkyl, cycloalkyl, amino, hydroxy, alkanoylamino, alkylamido, arylcarbonylamino, nitro, cyano, thiol and/or alkylthio, as well as any of the other substituents as defined for $R^6$.

Unless otherwise indicated, the term "lower alkynyl" or "alkenyl" as used herein by itself or as part of another group refers to straight or branched chain radicals of 2 to 40 carbons, preferably 2 to 20 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecenyl and the like, and which may be optionally substituted with 1 to 4 substituents, namely, halogen, alkyl, alkoxy, alkenyl, alkynyl, aryl, arylalkyl, cycloalkyl, amino, hydroxy, alkanoylamino, alkyl-amido, arylcarbonylamino, nitro, cyano, thiol, and/or alkylthio, as well as any of the other substituents as defined for $R^6$.

Examples of suitable $(CH_2)_p$ groups include

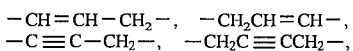

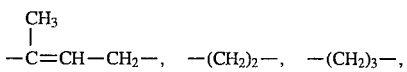

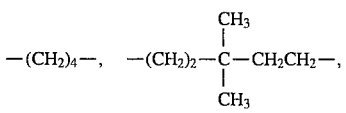

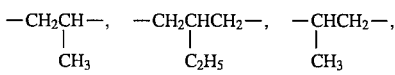

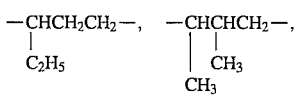

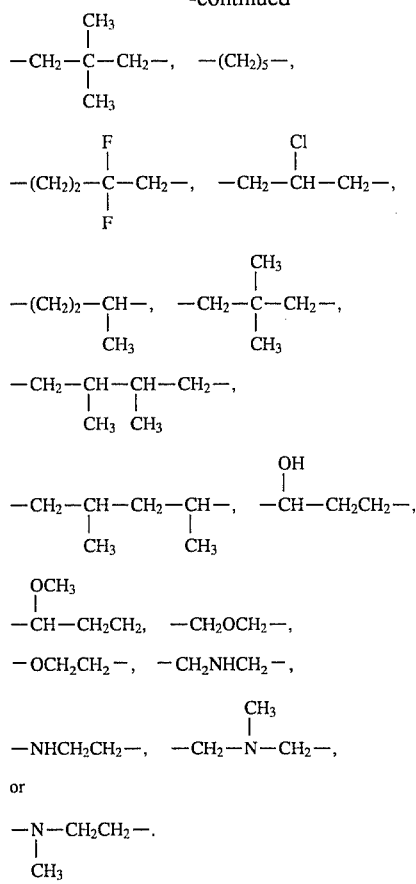

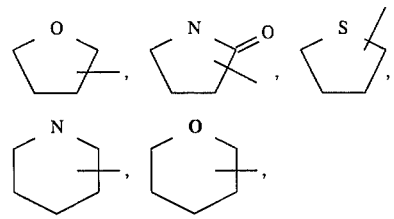

The term "halogen" or "halo" as used herein refers to chlorine, bromine, fluorine, and iodine as well as CF₃, with chlorine or fluorine being preferred.

The term "amino" as used herein refers to unsubstituted amino as well as monosubstituted amino or disubstituted amino wherein the substituents may be alkyl and/or aryl.

The term "metal ion" refers to alkali metal ions such as sodium, potassium or lithium and alkaline earth metal ions such as magnesium and calcium, as well as zinc and aluminum.

The term "cycloheteroalkyl" as used herein as an R¹ substituent refers to a 5-, 6- or 7-membered saturated ring which includes 1 to 2 hetero atoms such as nitrogen, oxygen and/or sulfur, linked to the carbon "C" of

through a carbon atom or a heteroatom, where possible, optionally via the linker CH₂)ₚ (which is defined above), such as

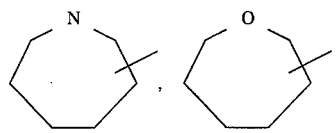

and the like. The above groups may include 1 to 3 substituents such as any of the R⁶ groups as defined above. In addition, any of the above rings can be fused to a cycloalkyl, aryl, heteroaryl or cycloheteroalkyl ring.

The term "heteroaryl" as an R¹ substituent refers to a 5- or 6- membered aromatic ring which includes 1, 2, 3 or 4 hetero atoms such as nitrogen, oxygen or sulfur, which is linked to the carbon "C" of

through a carbon atom or a heteroatom, where possible, optionally via the linker (CH₂)ₚ (which is defined above), such as

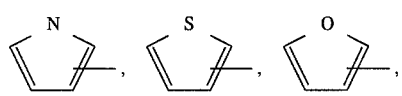

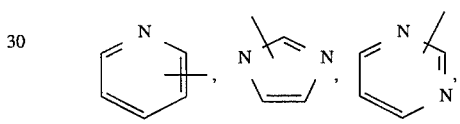

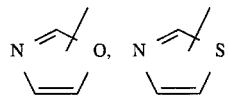

and the like. The above groups may include 1 to 3 substituents such as any of the R⁶ groups as defined above. In addition, any of the above rings can be fused to a cycloalkyl, aryl, heteroaryl or cycloheteroalkyl ring.

The term "cycloheteroalkylalkyl" as defined by R¹ refers to cycloheteroalkyl groups as defined above linked through a C atom or heteroatom to the "C" of

group through a (CH₂)ₚ chain wherein p is preferably 1 to 8.

The term "heteroarylalkyl" as defined by R¹ refers to a heteroaryl group as defined above linked through a C atom or heteroatom to the "C" of

through a —(CH₂)ₚ— chain as defined above, where p is preferably 1 to 8.

Preferred are compounds of formulae I and IA wherein R² is OR⁵ and R⁵ is a metal ion such as Na or K, or H or a pharmaceutically acceptable salt;

R³ is H, a metal ion such as Na or K;

R⁴ is a metal ion such as Na or K;

$R^1$ is alkenyl such as

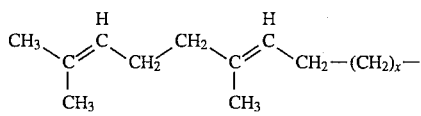

wherein $(CH_2)_x$ is defined as $(CH_2)_p$ above and x is preferably 2 to 8,

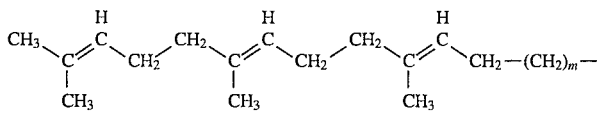

m is 1 to 5;

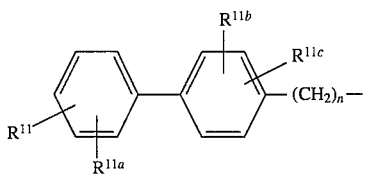

n=1 to 15;

$R^{11}$, $R^{11a}$, $R^{11b}$, and $R^{11c}$ are independently selected from H, alkyl such as propyl, halo, alkoxy, such as methoxy or propyloxy, alkenyl such as

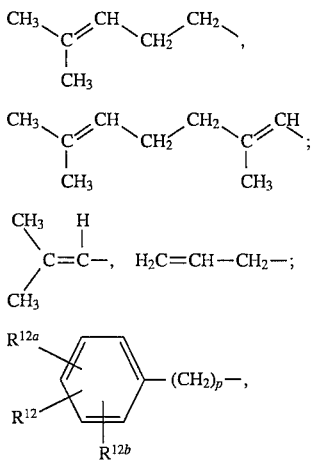

wherein $R^{12}$, $R^{12a}$ and $R^{12b}$ are independently selected from H, aryl (such as phenyl or naphthyl), alkylphenyl (such as p-propylphenyl, p-pentylphenyl), alkyl containing 1 to 20 carbons (such as p-heptyl), halo, alkoxy (such as methoxy or propyloxy), alkenyl (such as

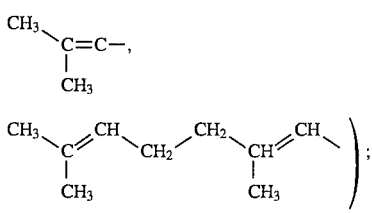

arylalkyloxy (such as phenethyloxy), alkenyloxy (such as

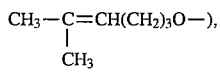

aryloxy (such as phenoxy), phenylalkyl (such as benzyl, phenylpropyl), alkylphenoxy (such as orthobutylphenoxy), alkenylphenyl (such as

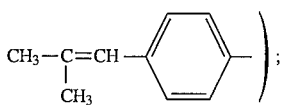

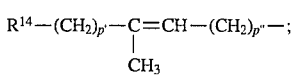

or

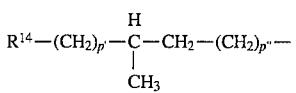

wherein $R^{14}$ is aryl, heteroaryl, aryloxy, heteroaryloxy, cycloalkyl, heterocycloalkyl, and $(CH_2)_{p'}$ and $(CH_2)_{p''}$ are as defined above for $—(CH_2)_p—$. Preferred p' and p" are independently 1 to 4;

$$Ar^1—O—Ar^2—(CH_2)_p—$$

$Ar^1$ and $Ar^2$ are independently selected from any of the Ar groups defined hereinbefore, and $(CH_2)_p$ is as defined hereinbefore, and p is preferably 2, 3, 4 or 5.

The compounds of the invention may be prepared according to the following reaction sequences.

General Schemes A and B for the Preparation of α-Phosphonosulfinates

Compounds of Formula I where $R^2$ is $OR^5$ or $R^{5a}$

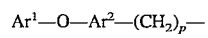

Scheme A

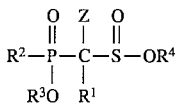

II

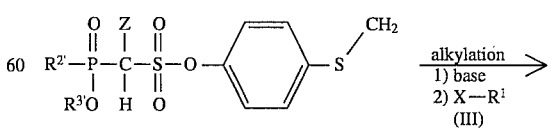

X = I, Br, Cl, tosylate, $CF_3SO_2O^-$

-continued

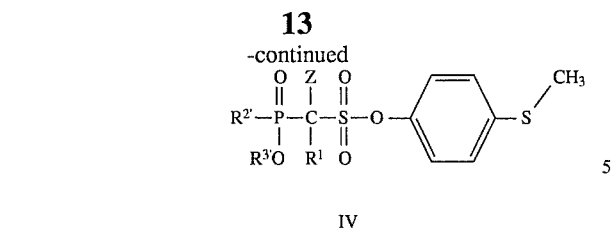
IV ($R^{3'}$ is alkyl, arylalkyl, aryl or cycloalkyl, and $R^{2'}$ is $R^{5a}$ or $OR^{5'}$ where $R^{5'}$ is alkyl, arylalkyl, aryl or cycloalkyl)

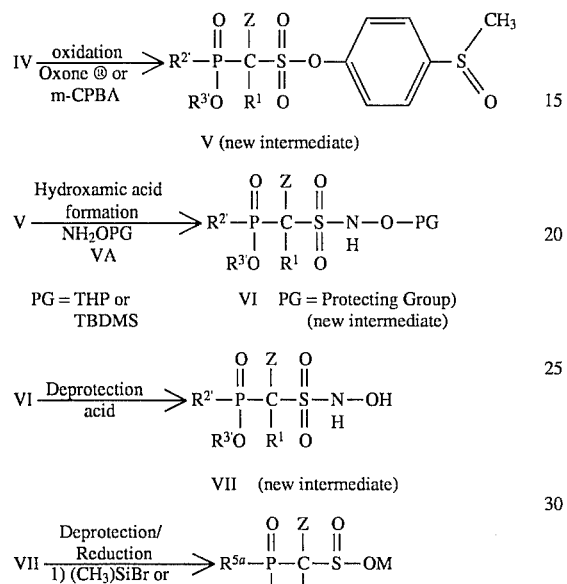

PG = THP or TBDMS   VI  PG = Protecting Group) (new intermediate)

VII (new intermediate)

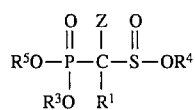

(where $R^2 = R^{5a}$)
IB' or

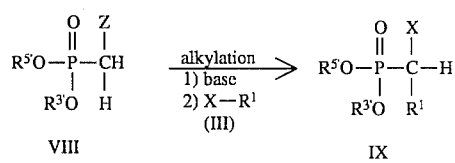

IA' (where $R^2 = R^5$)

M=H, metal ion or other pharmaceutically acceptable cation

Compounds of Formula I where $R^2$ is $OR^5$ $$R^5O-\underset{\underset{R^3O}{|}}{\overset{\overset{O}{\|}}{P}}-\underset{\underset{R^1}{|}}{\overset{\overset{Z}{|}}{C}}-\overset{\overset{O}{\|}}{\underset{\underset{}{\|}}{S}}-OR^4$$

Scheme B

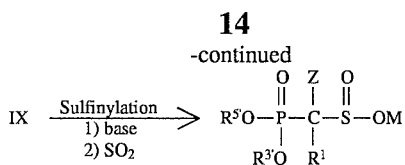

IX ($R^{3'}$ and $R^{5'}$ are independently alkyl, arylalkyl, aryl or cycloalkyl)

X = I, Br, Cl, tosylate, $CF_3SO_2O-$

-continued

IX 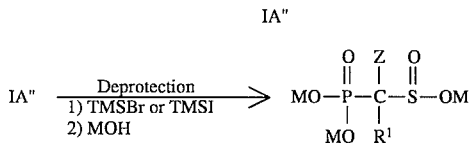
IA''

IA'' 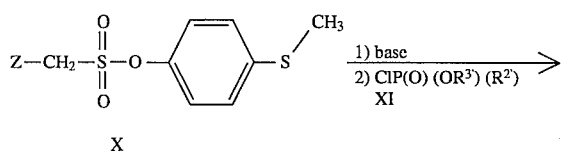
IA'

Reaction Schemes C and D

Preparation of Starting Phosphonosulfonate II for Scheme A

Scheme C

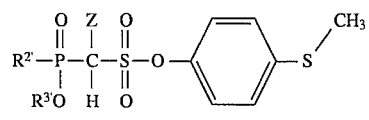
X

II

Scheme D
Alternatively, Z' can be incorporated after $R^1$ (where Z'=lower alkyl or halogen)

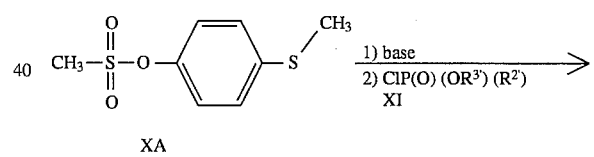
XA

XII

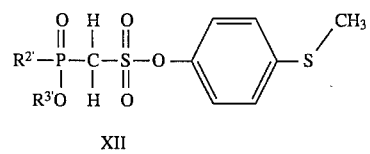
IIA

IIA 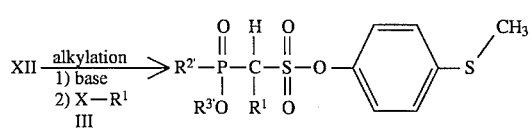

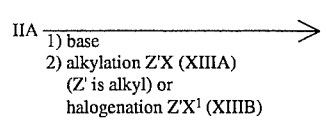

IIB (X¹ is Cl, I or Br or succinimido)
(Z' is Cl, I, or Br); or
where Z'=F, reagents used for fluorination include XeF₂,

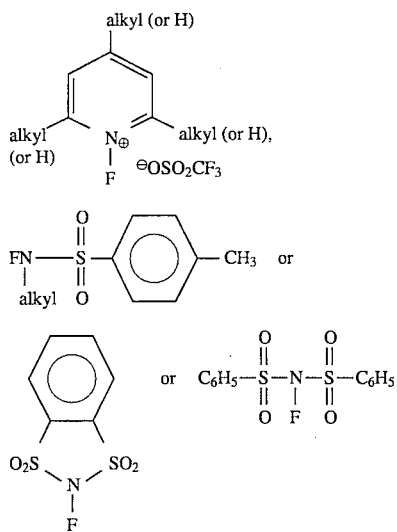

Reaction Scheme E
Preparation of Starting Compound VIII for Scheme B

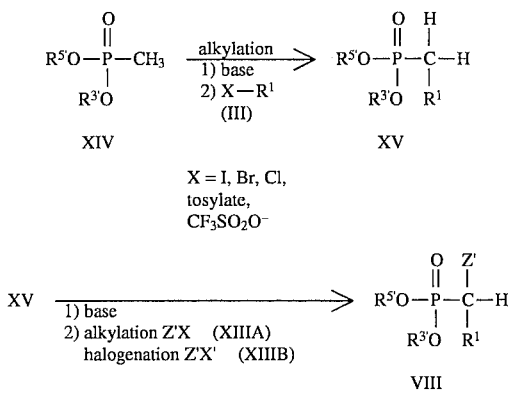

Scheme F
Synthesis of Monoesters

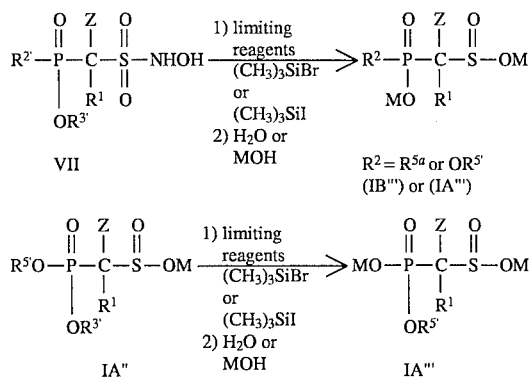

Referring to General Scheme A, compounds of the invention I where $R^2$ is $R^{5a}$ or OM and M is H, metal ion or other pharmaceutically acceptable cation, may be prepared by alkylating the phosphonosulfonate II by reacting II with compound III in the presence of an appropriate base and an inert organic solvent under an inert atmosphere to form IV.

In carrying out the above reaction, the phosphonosulfonate II is employed in a molar ratio to compound III of within the range of from about 5:1 to about 0.8:1, and preferably from about 3:1 to about 1.2:1. The reaction is carried out under an inert atmosphere, such as argon, preferably at a temperature of within the range of from about −78 to about 80° C., and more preferably from about 0 to about 50° C., although the reaction may be completed at room temperature.

Examples of inert organic solvents suitable for use herein include, but are not limited to dimethylformamide (DMF), tetrahydrofuran (THF), dimethylsulfoxide (DMSO), hexamethylphosphoramide (HMPA) or diethyl ether (Et₂O), or mixtures thereof.

Examples of bases suitable for use in carrying out the above reaction include, but are not limited to, alkali metal hydrides, such as sodium hydride (which is preferred), potassium hydride, lithium-, sodium- or potassium bis(trimethylsilyl)amide, lithium diisopropylamide or butyllithium.

Compound IV is subjected to oxidation by treating IV with an oxidant such as Oxone® (potassium peroxymonosulfate) in the presence of an alcohol solvent such as methanol, ethanol or isopropyl alcohol, which may contain water, and optionally a weak base such as NaHCO₃, NaCO₃ or K₂HPO₄; m-chloroperbenzoic acid (m-CPBA) in CH₂Cl₂ or CHCl₃; t-C₄H₉COOH, hydrogen peroxide or I₂/H₂O, at a temperature within the range of from about −20° to about 50° C., preferably from about −5° to about 25° C., to form V.

Compound V (which is a novel intermediate) is made to undergo hydroxamic acid formation by treating with amine VA

VA  NH₂OPG (where PG represents a protecting group) which can be O-tetrahydropyran-2-ylhydroxylamine (NH₂OTHP) or O-tert-butyldimethylsilylhydroxylamine (NH₂OTBDMS), in the presence of an inert organic solvent, such as toluene, chloroform, tetrahydrofuran or xylene, at a temperature within the range of from about 0° C. to about 140° C., preferably from about 25° to about 80° C., to form protected compound VI (which is a new intermediate). The amine VA will be employed in a molar ratio to V of within the range of from about 1:1 to about 15:1, preferably from about 3:1 to about 7:1.

The protecting group PG of compound VI is then removed by treating VI with a deprotecting agent such as pyridinium para-toluenesulfonate, p-toluenesulfonic acid or acetic acid, in the presence of a solvent such as methanol, ethanol or aqueous tetrahydrofuran, at a temperature within the range of from about 0° C. to about 70° C., preferably from about 20 to about 50° C., to form hydroxamic acid VII (which is a new intermediate). Hydroxamic acid VII is deprotected and reduced by treating VII with bromotrimethylsilane (TMSBr), or iodotrimethyl silane (TMSI) and the like, in the presence of an inert organic solvent such as methylene chloride, chloroform or dichloroethane, optionally in the presence of one or more additives such as allyl trimethylsilane, 2-methyl-2-butene, 2,4-6-collidine, hexamethyldisilazane ([(CH₃)₃Si]₂NH) , followed by treatment with water and/or a strong base, such as potassium hydroxide, sodium hydroxide, lithium hydroxide, ammonium hydroxide or calcium hydroxide, to form the phosphonosulfinate of the invention IA (or IA' or IB').

In carrying out the above deprotection/reduction to form IA' or IB', the silylating agent will be employed in a molar ratio to VII of within the range of from about 3:1 to about 30:1, preferably from about 8:1 to about 15:1 and the additive(s) will be employed in a molar ratio to VII of within the range of from about 1:1 to about 20:1, preferably from about 4:1 to about 15:1.

Referring to Scheme B, compounds of the invention IA" (where $R^2=OR^5$) and IA' may be prepared by alkylating the phosphonate VIII by metalating VIII with a base, such as n-butyllithium, sec-butyl-lithium, t-butyllithium, or lithium diisopropyl-amide, to form the lithium anion of VIII and alkylating the lithium anion of VIII by reacting with compound III to form IX.

In carrying out the above reaction, the base is employed in a molar ratio to the phosphonate VIII within the range of from about 1.4:1 to about 0.8:1, preferably about 1:1 and the phosphonate VIII is employed in a molar ratio to compound III of within the range of from about 2:1 to about 0.2:1, and preferably from about 1.5:1 to about 0.7:1. The reactions are carried out under an inert atmosphere, such as argon, initially preferably at a temperature of within the range of from about −90° to about 80° C., and more preferably from about −80° C. to about 50° C., although the reaction may be completed at room temperature. Bases and solvents appropriate for this reaction are as described for Scheme A.

Compound IX is sulfinylated by treating IX with base (such as described above with respect to formation of IX) and then with sulfur dioxide to form compound of the invention IA".

In carrying out the above reaction, the base is employed in a molar ratio to compound IX of within the range of from about 1.5:1 to about 0.8:1, and preferably about 1.1:1, and the sulfur dioxide is employed in excess. The reaction is carried out under an inert atmosphere, such as argon, initially preferably at a reduced temperature of within the range of from about −78° to about 80° C., and more preferably from about 0° to about 50° C., although the reaction may be completed at room temperature. Bases and solvents appropriate for this reaction are as described above with respect to the alkylation.

Compound IA" of the invention may be converted to compound IA' of the invention by treating IA" with a deprotecting agent such as $(CH_3)_3SiBr$ or $(CH_3)_3SiI$ followed by water or base, employing reactants, solvents and conditions as described with respect to Scheme A in the deprotection of VII to form compound of the invention IA'.

Referring to Scheme C, starting compounds of formula II may be prepared by reacting starting sulfonate X with a strong base such as any of those used in Schemes A or B, in the presence of or followed by reaction with chlorophosphate XI, and an inert organic solvent such as used in Schemes A or B, to form II.

In carrying out the reaction of Scheme C, chlorophosphate XI will be employed in a molar ratio to sulfonate X of within the range of from about 3:1 to about 1:2, and preferably from about 2.0:1 to about 1:1. The reaction is carried out at a temperature of within the range of from about −100° to about 30° C., and preferably from about −90° to about 0° C.

The above procedure for preparing II is similar to that described by Carretero, J. C.; Demillequand, M.; Ghosez, L., Tetrahedron, Vol. 43, 1987, pp 5125–5134.

Scheme D illustrates an alternative procedure for preparing starting material II wherein Z is incorporated after $R^1$, and Z is Z' which is lower alkyl or halogen. As seen in Scheme D, compound XA is treated with base followed by XI, employing the reaction conditions described in Scheme C., to form phosphonosulfonate XII which is alkylated by treatment with base and compound III (as described in the conversion of II to IV in Scheme A) to form phosphonosulfonate IIA.

Phosphonosulfonate IIA is then treated with base and then alkylated with alkyl halide XIIIA or halogenated with XIIIB to form IIB. The alkylation or halogenation step is as described in the alkylation of II to IV in Scheme A or VIII to IX in Scheme B.

Referring to Scheme E, starting compound VIII employed in Scheme B is prepared from compound XIV which is alkylated by treatment with base and III (employing procedures as described with respect to the alkylation of VIII to IX in Scheme B) to form compound XV. Compound XV is then treated with base and alkylated or halogenated employing procedures as described with respect to conversion of IIA to IIB in Scheme D.

Referring to Scheme F, VII or IA" may be deprotected selectively to monoesters IB'" or IA'" by reacting with limiting quantities (preferably 1–3 equivalents) of deprotecting agents such as $(CH_3)_3SiBr$ or $(CH_3)_3SiI$, optionally in the presence of the additives listed above.

Examples of starting alkylating agents that is $R^1X$ or $R^1Hal$ suitable for use herein include the following which are either known in the literature or are simple derivatives of known compounds prepared by employing conventional procedures.

It will be appreciated that the $R^1X$ compounds listed in the following table represent all possible stereoisomers.

$R^1Hal$ where Hal is Cl, Br or I, or Otosyl or $OSO_2CF_3$ is as follows in A. through F.

A.

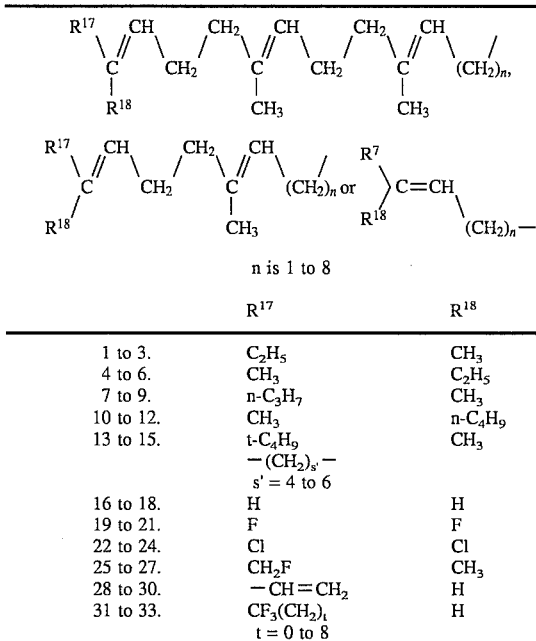

n is 1 to 8

| | $R^{17}$ | $R^{18}$ |
|---|---|---|
| 1 to 3. | $C_2H_5$ | $CH_3$ |
| 4 to 6. | $CH_3$ | $C_2H_5$ |
| 7 to 9. | n-$C_3H_7$ | $CH_3$ |
| 10 to 12. | $CH_3$ | n-$C_4H_9$ |
| 13 to 15. | t-$C_4H_9$ —$(CH_2)_{s'}$— s' = 4 to 6 | $CH_3$ |
| 16 to 18. | H | H |
| 19 to 21. | F | F |
| 22 to 24. | Cl | Cl |
| 25 to 27. | $CH_2F$ | $CH_3$ |
| 28 to 30. | —CH=$CH_2$ | H |
| 31 to 33. | $CF_3(CH_2)_t$ t = 0 to 8 | H |

B.

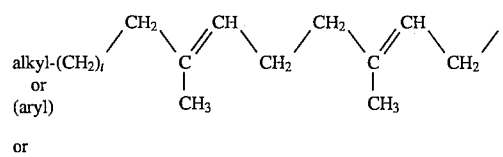

or

-continued $$\text{alkyl-}(CH_2)_t \text{ or (aryl)} - CH_2 - \underset{CH_3}{\underset{|}{C}} = CH - CH_2 - \quad (n \text{ is } 1 \text{ to } 8)$$

34–35. $CH_3(CH_2)_t-$ where t is 0 to 8

36–37. $\underset{CH_3}{\underset{|}{\overset{CH_3}{\overset{|}{C}}}}-(CH_2)_t-$ where t is 0 to 8

38–39. R—⟨phenyl⟩—$(CH_2)_t$ where t is 0 to 8

C. Miscellaneous

40–41. R—⟨cyclohexyl⟩—$(CH_2)_t-$ where t is 0 to 8

42. R—⟨pyridyl-N⟩—$(CH_2)_t-$

43. R—⟨thiophene-S⟩—$(CH_2)_t-$

44. $R_1$—⟨naphthyl⟩—$R_2$—$(CH_2)_t-$

45. $R_1$—⟨naphthyl⟩—$R_2$ , $(CH_2)_2-$

46. $CF_3(CH_2)_t-$

47. $\underset{CF_3}{\underset{|}{\overset{CF_3}{\overset{|}{CH}}}}-(CH_2)_t-$

48. $R_3$—⟨phenyl⟩—$O-(CH_2)_t-$

49. $R_3$—⟨phenyl⟩—$\underset{|}{\overset{H}{N}}-(CH_2)_t-$

50. $R_3$—⟨phenyl⟩—$S-(CH_2)_t-$

51. $R_3$—⟨pyridyl-N⟩—$O-(CH_2)_t-$

52. ⟨(CH$_2$)$_x$ ring⟩—$(CH_2)_t$

Examples 42 to 47, t=0 to 8 $R_1$, $R_2$ and $R_3$ may be the same or different and can be any of the radicals included in $R^6$.

Examples 48 to 52 t=1 to 8 x=3 to 8

53. $CH_3-\underset{|}{\overset{CH_3}{\overset{|}{C}}}=C-CH_2+CH_2-\underset{|}{\overset{CH_3}{\overset{|}{C}}}=C-CH_2\overset{}{)_{\overline{t}}}(CH_2)_n-$ t = 0, 1, 2, 3     n = 0 to 8

54. $H-\underset{CH_3}{\underset{|}{\overset{CH_3}{\overset{|}{C}}}}-CH_2-CH_2+CH_2-\overset{CH_3}{\overset{|}{CH}}-CH_2-CH_2\overset{}{)_{\overline{t}}}(CH_2)_n-$ t = 0, 1, 2, 3     n = 0 to 8

D.

$$CH_3\underset{R^{21}}{\underset{|}{\overset{}{C}}}\overset{CH}{\overset{\diagup\diagdown}{}}\underset{CH_2}{}\overset{CH_2}{\diagup\diagdown}\underset{R^{22}}{\underset{|}{\overset{}{C}}}\overset{CH}{\overset{\diagup\diagdown}{}}\underset{CH_2}{}\overset{CH_2}{\diagup\diagdown}\underset{R^{23}}{\underset{|}{\overset{}{C}}}\overset{CH}{\overset{\diagup\diagdown}{}}(CH_2)_n \text{ or}$$

n = 1 to 8

$$CH_3\underset{R^{21}}{\underset{|}{\overset{}{C}}}\overset{CH}{\overset{\diagup\diagdown}{}}\underset{CH_2}{}\overset{CH_2}{\diagup\diagdown}\underset{R^{22}}{\underset{|}{\overset{}{C}}}\overset{CH}{\overset{\diagup\diagdown}{}}(CH_2)_n$$

n = 1 to 8

| | $R^{21}$ | $R^{22}$ | $R^{23}$ |
|---|---|---|---|
| 55–56. | $C_2H_5$ | $C_2H_5$ | $CH_3$ |
| 57–58. | $CH_3$ | $CH_3$ | $C_2H_5$ |
| 59–60. | $CH_3$ | $C_2H_5$ | $C_2H_5$ |
| 61–62. | $C_2H_5$ | $C_2H_5$ | $C_2H_5$ |
| 63–64. | $CH_3$ | $C_2H_5$ | $CH_3$ |
| 65–66. | $CH_3$ | H | $CH_3$ |
| 67–68. | $CH_3$ | $CH_3$ | H |
| 69–70. | H | H | H |
| 71–72. | $CF_3$ | $CH_3$ | $CH_3$ |
| 73–74. | $CH_3$ | $CF_3$ | $CH_3$ |
| 75–76. | $CH_3$ | $CH_3$ | $CF_3$ |
| 77–78. | $CF_3$ | $CF_3$ | $CH_3$ |
| 79–80. | $CF_3$ | $CF_3$ | $CF_3$ |

E.

$$CH_3\underset{CH_3}{\underset{|}{\overset{}{C}}}\overset{CH}{\overset{\diagup\diagdown}{}}\underset{CH_2}{}\overset{CH_2}{\diagup\diagdown}\underset{CH_3}{\underset{|}{\overset{}{C}}}\overset{CH}{\overset{\diagup\diagdown}{}}\underset{CH_2}{}\overset{CH_2}{\diagup\diagdown}\underset{R^{26}}{\underset{|}{\overset{R^{24}}{C}}}\overset{R^{25}}{\overset{|}{\overset{}{C}}}\overset{}{\diagup}(CH_2)_n \text{ or}$$

n = 1 to 8
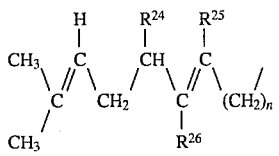
| | $R^{24}$ | $R^{25}$ | $R^{26}$ |
|---|---|---|---|
| 81-82. | H | I | H |
| 83-84. | H | H | I |
| 85-86. | H | $CH_3$ | $CH_3$ |
| 87-88. | $CH_3S$ | $CH_3$ | H |
| 89-90. | F | $CH_3$ | H |
| 91-92. | $CH_3$ | $CH_3$ | H |
| 93-94. | H | $CH_3$ | $CH_3$ |
| 95-96. | H | $CH_3$ | Cl |
| 97-98. | H | $CF_3$ | H |
| 99-100. | H | Cl | H |
| 101-102. | H | $CH_3$ | $(CH_3)_3Si$ |
| 103-104. | H | $CH_3$ | F |
| 105-106. | H | $CF_3$ | $CH_3$ |
| 107-108. | H | $CH_3$ | $CF_3$ |
In Examples 114 and 115, m is 0 to 8.
F. Other examples of $R^1$ include the following
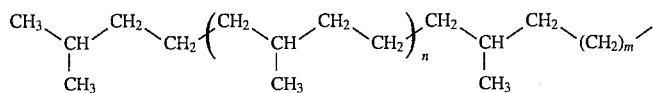 109.
(n is 0, 1)
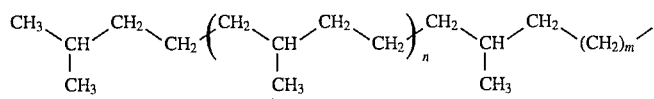 110.
(n is 0, 1)
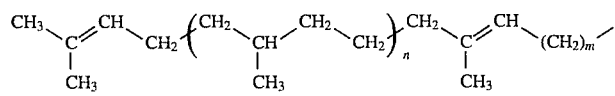 111.
(n is 0, 1)
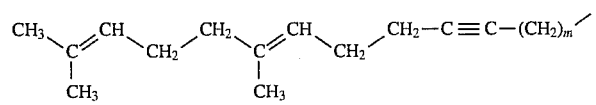 112.
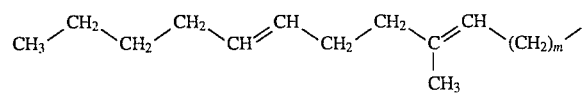 113.
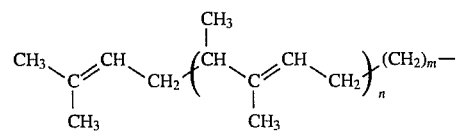 114.
(n is 1, 2)
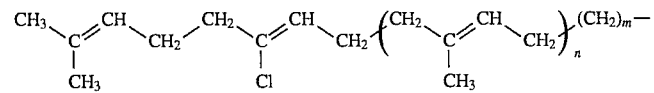 115.
(n is 0, 1)
In Examples 109 to 113, m is 1 to 8.

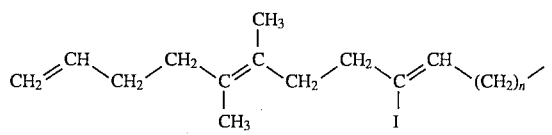 116.
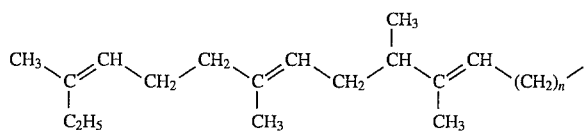 117.
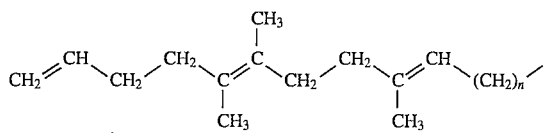 118.
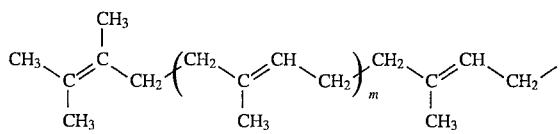 119.
(m is 1, 2)
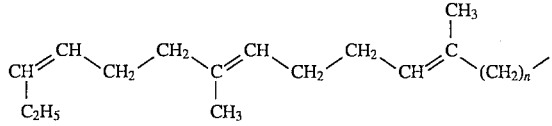 120.
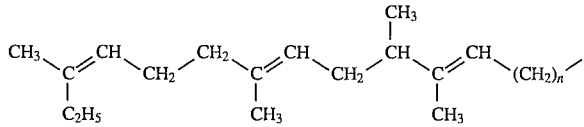 121.
In Examples 116 to 121, n is 1 to 8.
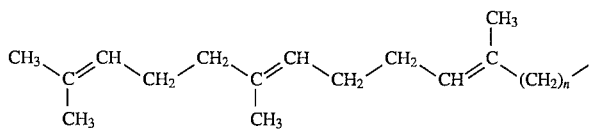 122.
(n is 1 to 8)
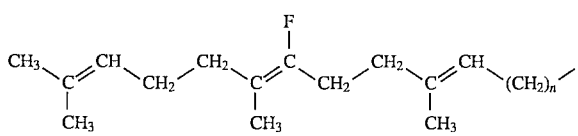 123.
(n is 1 to 8)
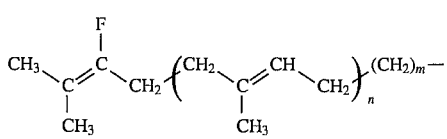 124.
(n is 1, 2)
(m is 0 to 8)
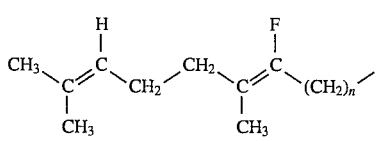 125.

(n is 1 to 8)

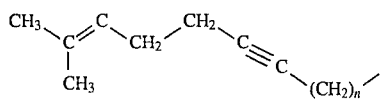

(n is 1 to 8)

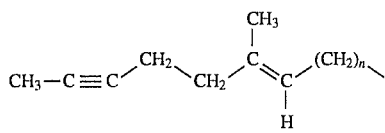

(n is 1 to 8)

$CH_3-C\equiv C-(CH_2)_n-$  (n = 4–12)

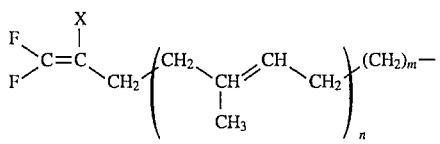

X=H, F, $CH_3$
n is 1 or 2
m is 0 to 8

$CH_3-C\equiv C-(CH_2)_n-C\equiv C-(CH_2)_m-$  130.

(n = 0–10)
(m is 0 to 8)

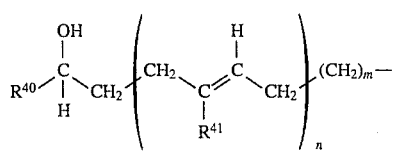

(n is 1 to 3)
(m is 0 to 8)

$R^{40}$=H, alkyl, cycloalkyl, or aryl such as methyl, ethyl, isopropyl, pentyl, phenyl and cyclopentyl
$R^{41}$=alkyl such as methyl, ethyl or halo such as Cl or F

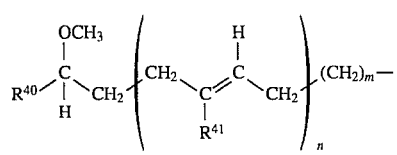

(m is 1 to 8)
(n is 1 to 3)

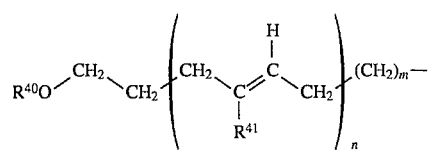

(m is 1 to 8)
(n is 1 to 3)

126.

127.

128.

129.

131.

132.

133.

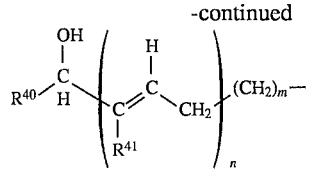

(m is 0 to 8)
(n is 1 to 3)

133a.

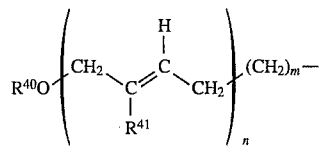

(m is 0 to 8)
(n is 1 to 3)

133b.

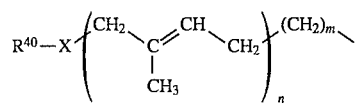

(m is 0 to 8)
(n is 1 to 3)
(X IS O, S, NH)

133c.

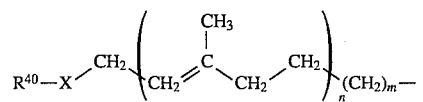

(X is O, S, NH, $CH_2$)
(m is 1 to 8)
(n is 1 to 3)

133d.

Following the procedures set out in the working Examples and described herein, the above starting materials may be employed to prepare compounds of the invention 1 to 133 wherein $R^3$, $R^4$ and $R^{5a}$ are independently H, alkyl, arylalkyl, cycloalkyl, metal ion or other pharmaceutically acceptable cations or salts, and $OR^5$ is Ometal, Ohio, Oalkyl, Oarylalkyl, Ocycloalkyl.

Additional compounds within the scope of the present invention are set out below.

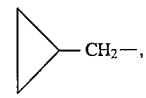

| | $R^{42}$ | $R^{43}$ | $R^{44}$ | $R^{45}$ | $R^{46}$ | t |
|---|---|---|---|---|---|---|
| 134) | H | H | H | H | n-$C_3H_7$ | 3 |
| 135) | H | H | H | H | n-$C_4H_9$ | 3 |
| 136) | H | H | H | H | $(CH_3)_2$—C=CH— | 4 |
| 137) | H | H | H | H | $(CH_3)_2$—C=CH—$CH_2$— | 2 |
| 138) | $CH_3$ | H | $CH_3$ | H | ▷—$CH_2$— | 3 |
| 139) | H | H | $CH_3$ | H | $(CH_3)_2$—CH—$CH_2$—O— | 3 |
| 140) | H | $CH_3$ | $CH_3$ | H | n-$C_3H_7$ | 3 |
| 141) | $CH_3O$ | H | H | H | n-$C_4H_9$ | 3 |
| 142) | H | H | H | H | $(CH_3)_2$—C=CH— | 3 |
| 143) | H | H | H | H | $(CH_3)_2$—C=CH—$CH_2$— | 4 |
| 144) | $CH_3$ | H | H | H | ▷—$CH_2$— | 5 |
| 145) | F | H | $CH_3$ | H | n-$C_3H_7$ | 3 |
| 146) | $CH_3$ | H | F | H | n-$C_4H_9$ | 3 |
| 147) | H | $CH_3$ | H | $CH_3$ | $(CH_3)_2$—C=CH— | 3 |
| 148) | H | H | H | $CF_3$ | $(CH_3)_2$—C=CH—$CH_2$— | 3 |
| 149) | H | H | H | F | ▷—$CH_2$— | 3 |
| 150) | H | Cl | Cl | H | $CH_2$=CH—$CH_2$— | 3 |
| 151) | $CH_3$ | H | H | H | $C_4H_9$ | 3 |
| 152) | H | H | OH | H | $C_3H_7$ | 3 |
| 153) | H | H | $OCH_3$ | H | $C_3H_7$ | 4 |
| 154) | H | H | $CH_3$ | H | $C_3H_7$ | 3 |
| 155) | H | OH | H | H | $C_3H_7$ | 3 |
| 156) | H | $OCH_3$ | H | H | $C_3H_7$ | 4 |
| 157) | H | $CH_3$ | H | H | $C_3H_7$ | 3 |

$R^2$=H, OMetal, alkyl, aryl $R^3$=H, metal ion or alkyl $R^4$=H or metal ion

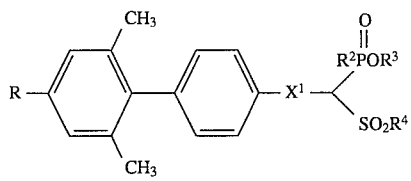
158)

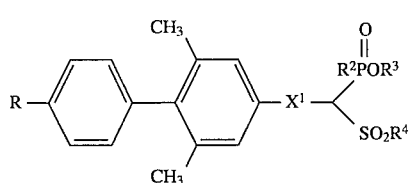
159)

$X^1$ = —$(CH_2)_n$—, —CH=CH—$CH_2$—
n = 1 to 6

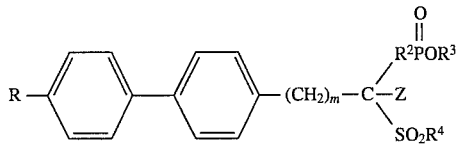
160)

Re 158) to 160)

R is n—$C_3H_7$, n—$C_4H_9$, $(CH_3)_2$—C=CH—, $CH_3$—CH=CH—$CH_2$—, $(CH_3)_2$—CH=CH—$CH_2$—, $CH_2$=CH—$CH_2$O—, $(CH_3)_2$—CH—O—, $(CH_3)_2CHCH_2O$—,

▷—$CH_2$—, $CH_2$=CH—$CH_2$—, $CH_2$=CH—$CH_2CH_2$—, phenyl, pyridyl

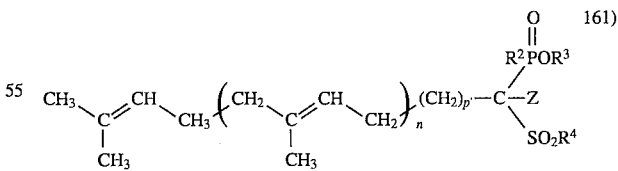
161)

Z=Cl, F, alkyl such as methyl, ethyl, propyl or allyl n=0, 1, 2

$p^1$=0–8 m=2–8

In compounds 158) to 161)

$R^3$=H, metal ion or alkyl $R^4$=H, metal ion $R^2$=OH, Ometal, alkyl, aryl

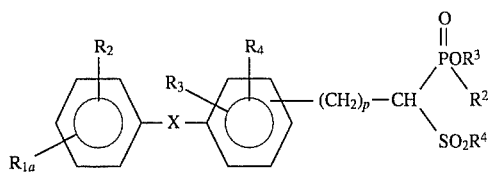
162)

X is O, S, NH, SO, $SO_2$, $CR_5R_6$, C=O $R_{1a}$, $R_3$, $R_4$, $R_5$ and $R_6$ are independently H, halogen, $C_1$–$C_5$alkyl, $C_1$–$C_5$alkenyl, $C_1$–$C_5$alkoxy, aryl, arylalkyl, aryloxy; for $R_5$ and $R_6$, halogen can be fluorine only; and $R^2$, $R^3$ and $R^4$ are as defined previously.

Examples of the compounds within the scope of the invention are set out below.

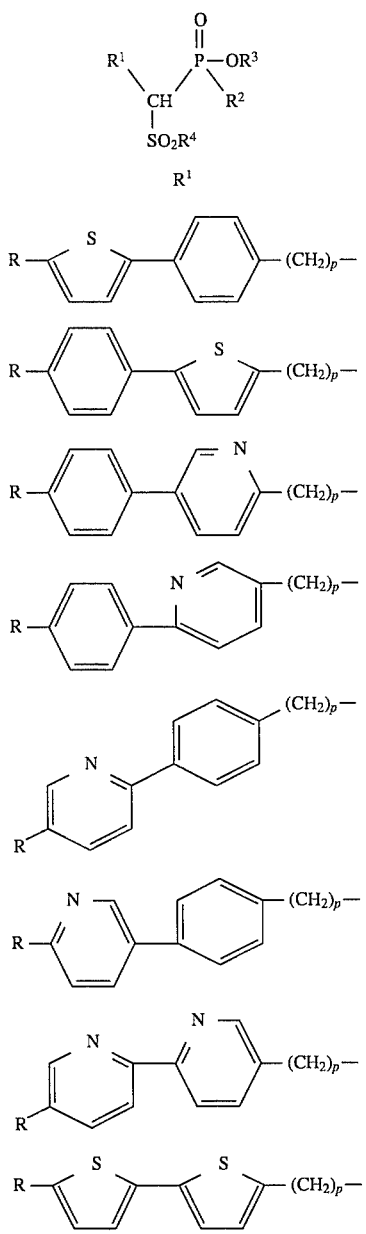

163)

164)

165)

166)

167)

168)

169)

170)

R is as defined for 158) to 160).

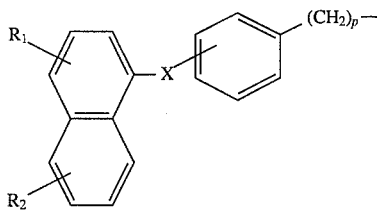
171)

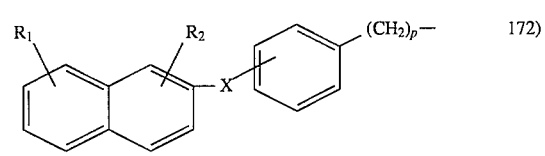
172)

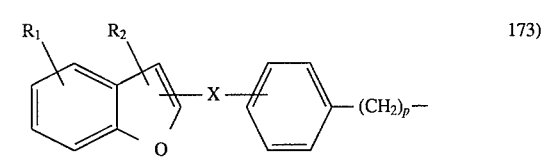
173)

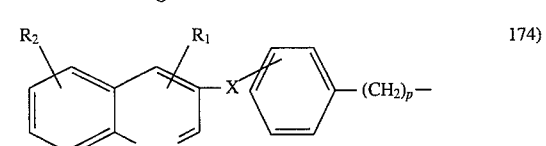
174)

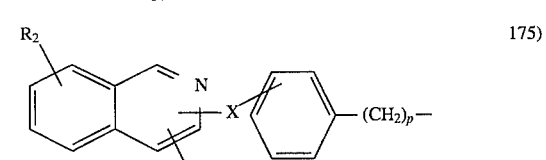
175)

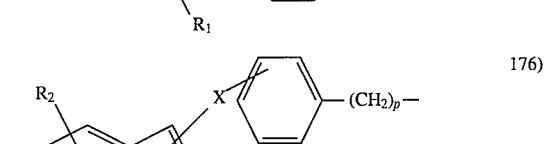
176)

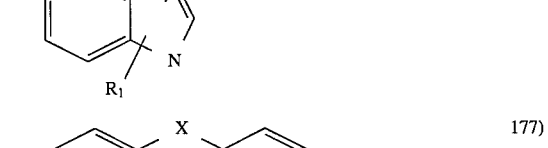
177)

X=bond, O, NH, S, $CH_2$, $CR_5R_6$ p=1 to 8 n=0 to 4; $R_1$, $R_2$, $R_5$ and $R_6$ are independently halogen, alkyl, alkenyl, alkoxy, aryl, H, aryloxy; for $R^5$ and $R^6$ halogen can be fluorine only, and $R^2$, $R^3$ and $R^4$ are as defined hereinbefore.

Preferred are compounds of the formula

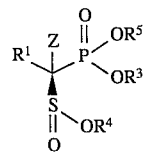

wherein Z is H, $R^1$ is preferably $Ar^1$—O—$Ar^2$—$(CH_2)_p$—, $R^3$, $R^5$ and $R^4$ are H or an alkali metal such as K or Na.

More preferred are compounds of formula IS where $R^1$ is

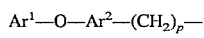
$Ar^1—O—Ar^2—(CH_2)_p—$ (p is 2, 3, 4 or 5) $R^4$ is an alkali metal such as K or Na, Z is H.

The compounds of Formula I of the invention inhibit cholesterol biosynthesis by inhibition of de novo squalene production. These compounds inhibit the squalene synthetase enzyme and, in addition, some of the compounds of Formula I of the invention inhibit other enzymes in the pathway from isopentenyl diphosphate to squalene, that is, farnesyl diphosphate synthetase and isopentenyl diphosphatedimethylallyl diphosphate isomerase.

The compounds of the invention are useful in treating hyperlipoproteinemia, hyperlipidemia, hypercholesterolemia, hypertriglyceridemia, combined hypercholesterolemia and hypertriglyceridemia, and/or in preventing development of and/or treating atherosclerosis. Thus, the compounds of the invention may De used to treat diseases such as chylomicronemia syndrome, Type I hyperlipoproteinemia, familial combined hyperlipoproteinemia, familial hypermriglyceridemia, mixed hyperlipoproteinemia, familial hypercholesterolemia and Type III hyperlipoproteinemia and/or atherosclerosis.

In addition, the compounds of the invention may increase plasma high density lipoprotein cholesterol levels.

The compounds of the invention may also be useful in inhibiting formation of gallstones, treating hepatitis D (by virtue of protein prenyltransferase inhibition, Glenn et al, Science, Vol. 256, pp. 1331–1333, May 29, 1992), treating tumors, lowering blood pressure, lowering blood sugar, treating diabetes mellitus, treating inflammation, as a diuretic, as an inotropic agent, as an anti-arthritic (antirheumatic) agent, in treating other diseases of calcium and phosphate metabolism including treatment of bone resorption, Paget's disease, osteoporosis, calcification of joints, implants and metastasis, as antitartar and anticalculus agents in toothpastes and mouthwashes, treating various stones and calculi, treating sickle cell anemia, treating hypoxia and ischemic tissue, and as an anti-ameobal agent, as well as for use in complexes with technetium-99 m and radioiodinated derivatives for use as diagnostics.

U.S. application Ser. No. 774,957, filed Oct. 11, 1991, discloses that post-translational modification of CAAX box containing proteins may be inhibited by administering a protein-prenyl transferase inhibitor which inhibits the transfer of the prenyl group [such as farnesyl (in the case of ras oncogene products), geranyl or geranylgeranyl] to the cysteine of the CAAX box by the protein-prenyl transferase enzyme. The protein-prenyl transferase inhibitor will block the protein-prenyl transferase enzyme from catalyzing the transfer of the prenyl group (for example, farnesyl, geranyl or geranyl-geranyl) from the prenyl pyrophosphate to the cys residue of the CAAX box, such as the ras p21 cys, or to the CAAX box cysteine of other CAAX box containing proteins. In the case of ras p21 oncogene products, inasmuch as the cys is not farnesylated, in the presence of the protein prenyl transferase inhibitor, it cannot effect interaction of the ras protein with the membrane so that neoplastic transformation of the cell will be prevented. In this manner proteinprenyl transferase inhibitors prevent neoplastic transformation of the cell, thereby acting as an anti-cancer agent for the treatment of and/or prevention of ras-related tumors.

Examples of CAAX box containing proteins which have been demonstrated or are believed to undergo prenylation include, but are not limited to, ras, nuclear lamins, α or γ subunits of heterotrimeric G-proteins, γsubunits of retinal transducin, G25K and K-rev p21, and protein families including rho, rap, rac, ral, and rab.

The present invention includes a method for blocking or preventing the prenylation of CAAX box containing proteins such as ras oncogene products, and thereby inhibit disease promoting effects of the CAAX box containing protein or more specifically prevent and/or treat ras-related tumors, by administering to a patient in need of treatment a therapeutic amount of a compound of Formula I of the invention which serves as a protein-prenyl transferase inhibitor.

The Formula I protein-prenyl transferase inhibitors, unlike HMG CoA reductase inhibitors, will interfere with prenylation of the ras oncogene products and inhibit their transforming activity, yet may or may not interfere with the synthesis of FPP, a precursor in the synthesis of ubiquinones, dolichols and Haem A.

The compounds of the invention may also be employed in combination with an antihyperlipoproteinemic agent, hypocholesterolemic agent, and/or hypotriglyceridemic agent, and/or antiatherosclerotic agent such as one or more HMG CoA reductase inhibitors, for example, pravastatin, lovastatin, simvastatin, velostatin, fluvastatin, rivastatin, atorvastatin, compactin, SDZ-63,370 (Sandoz), CI-981 (W-L), HR-780, L-645,164, CL-274,471, dalvastatin, α-, β-, and γ-tocotrienol, (3R, 5S, 6E)-9,9-bis(4-fluorophenyl)-3,5-dihydroxy-8-(1-methyl-1H-tetrazol-5-yl)-6,8-nonadienoic acid, L-arginine salt, (S)-4-[[2-[4-(4-fluorophenyl)-5-methyl-2-(1-methylethyl)-6-phenyl-3-pyridinyl]ethenyl]hydroxy-phosphinyl]-3-hydroxy-butanoic acid, disodium salt, BB-476, (British Biotechnology), dihydrocompactin, [4R-[4α, 6β(E)]]-6-[2-[5-(4-fluorophenyl)-3-(1-methylethyl)-1-(2-pyridinyl)-1H-pyrazol-4-yl]ethenyl]tetrahydro-4-hydroxy-2H-pyran-2-one, and/or 1H-pyrrole-1-heptanoic acid, 2-(4-fluorophenyl)-α, β-dihydroxy-5-(1-methylethyl)-3-phenyl-4-[(phenylamino)carbonyl]-calcium salt[R-(R*, R*)]; one or more fibric acid derivatives such as clofibrate, bezafibrate, Lopid(gemfibrozil) one or more other cholesterol biosynthesis inhibitors, such as NB-598, N-(1-oxododecyl)-4α10-dimethyl-8-aza-trans-decal-3β-ol, 2,4-undecadienoic acid, 11-[3-(hydroxymethyl)-4-oxo-2-oxetanyl]-3,5,7-trimethyl-, [2R-[2α(2E,4E,7R*),3β]]; one or more bile acid sequistrants, for example, cholestyr-amine, colestipol, polidexide (DEAE-Sephadex); one or more antioxidants, for example probucol and Vitamin E; and/or,one or more other lipid lowering and/or antiatherosclerotic agents, for example nicotinic acid or derivatives thereof, neomycin, p-aminosalicylic acid, probucol, hydroxypropylmethylcellulose, LS-2904, ethanol, 2[[1-methyl-2-[3-(trifluoromethyl)phenyl]ethyl]amino]-benzoate (ester).

The above compounds to be employed in combination with the squalene synthetase inhibitor of the invention will be used in amounts as indicated in the Physicians' Desk Reference (PDR).

The compounds of the invention may also be employed with sodium lauryl sulfate of other pharmaceutically acceptable detergents to enhance oral bioavailability of such compounds.

Inhibition of squalene synthetase may be measured by the following procedure.

Rat liver microsomal squalene synthetase activity is measured using farnesyl diphosphate as substrate and quantitating squalene synthesis using gas chromatographic analysis. The assay was developed by modifying conditions originally described by Agnew (Methods in Enzymology 110:357, 1985).

A further aspect of the present invention is a pharmaceutical composition consisting of at least one of the compounds of the invention, such as Formula I, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc., by an oral route, for example, in the form of tablets, capsules, granules or powders, or they can be administered by a parenteral route in the form of injectable preparations. The dose for adults is preferably between 200 and 2,000 mg per day, which can be administered in a single dose or in the form of individual doses from 1–4 times per day.

A typical capsule for oral administration contains active ingredient (250 mg), lactose (75 mg) and magnesium stearate (15 mg). The mixture is passed through a 60 mesh sieve and packed into a No. 1 gelatin capsule.

A typical injectable preparation is produced by asceptically placing 250 mg of sterile active ingredient into a vial, asceptically freeze-drying and sealing. For use, the contents of the vial are mixed with 2 mL of physiological saline, to produce an injectible preparation.

The following Examples represent preferred embodiments of the present invention.

Introduction to Experimental

All temperatures are reported in degress Centigrade.

$^1$H and $^3$C chemical shifts are reported as δ= values with respect to Me$_4$Si (δ=0). $^{31}$P spectra were obtained using 85% H$_3$PO$_4$ as an external reference (δ=0). Coupling constants J are reported in Hz. For mass spectra (mass spec or MS) value utilized for the parent M is that of the salt form which was prepared and tested.

All reactions were carried out under an atmosphere of dry argon or nitrogen. The following reagents and solvents were distilled prior to use from the indicated drying agents, where applicable: CH$_2$Cl$_2$, hexamethyl disilazane, and diisopropylamine (CaH$_2$); THF and diethyl ether (K, benzophenone), oxalyl chloride. Benzene was passed through neutral alumina (activity I) and stored over 4A-molecular sieves. Lithium bromide was dried at 100° C. over P$_2$O$_5$.(E,E)-Farnesol was purchased from Aldrich Chemical Company.

TLC was performed on E. Merck Silica Gel 60 F-254 plates (0.25 mm) or E. Merck Cellulose F plates (0.1 mm). Flash chromatography was carried out using E. Merck Kieselgel 60 (230–400 mesh).

Reverse-phase chromatographic purification of salts or mixed ester salts was carried on CHP20P gel or SP207SS gel, highly porous, polystyrene-divinyl benzene copolymers available from Mitsubishi Chemical Industries. The indicated general procedure was followed: An FMI Model RP-SY pump was utilized for solvent delivery. A column of CHP20P or SP207SS (2.5 cm diameter, 12–22 cm height) ws slurry packed and washed with water (500–1000 mL), and a basic, aqueous solution of the crude salt was applied to the top of the column. Typically, the column was eluted with water, followed by a gradient composed of increasing concentrations of acetonitrile or methanol in water. The gradient was created by placing the tip of a tightly stoppered separatory funnel containing 300–500 mL of the organic solvent, or an aqueous-organic mixture, just beneath the surface of a reservoir containing 300–500 mL of pure water. To start the gradient, the stopcock of the separatory funnel was opened, so that as the solvent was withdrawn by the pump from the reservoir, it was replaced with the solvent from the separatory funnel. HPLC-grade solvents were employed. Fractions were collected (10–15 mL each) at a flow rate of 5–10 mL per minute. Those fractions that contained pure product as judged by TLC or HPLC were pooled, the organic solvents were evaporated and the aqueous residue was lyophilized to dryness.

EXAMPLE 1

3-Phenoxy-α-phosphonobenzenebutanesulfinic acid, tripotassium salt

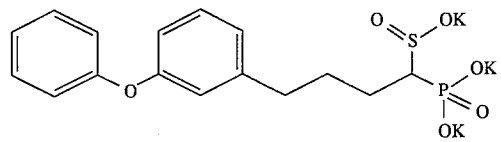

A. (E)-3-(3-Phenoxyphenyl)-2-propenoic acid, ethyl ester

Triethyl phosphonoacetate (6.5 mL, 32.8 mmol) was added dropwise to a suspension of sodium hydride (0.73 g, 30.2 mmol) in THF (40 mL) at 0° C. under argon. The ice bath was removed and the suspension was stirred at RT for 20 min, at which time a clear colorless solution resulted. The reaction solution was recooled to −78° C. and a solution of 3-phenoxybenzaldehyde (5.0 g, 25.2 mmol) in THF (10 mL) was added dropwise. The reaction mixture was stirred at −78° C. for 45 min. After warming to RT, the reaction was quenched with saturated ammonium chloride solution. Diethyl ether (200 mL) was added, the organic layer was washed with H$_2$O (50 mL), brine (50 mL) and dried over MgSO$_4$. Evaporation gave 4.0 g of title ester (96%) as a colorless oil.

B. 3-Phenoxybenzenepropanoic acid, ethyl ester

A mixture of Part A ester (6.5 g, 24.3 mmol) and palladium on carbon (10%, 300 mg) in ethyl acetate (50 mL) was stirred under a hydrogen atmosphere (balloon) overnight at RT. The reaction mixture was filtered through Celite. Evaporation of filtrate gave a crude oil. Purification was performed by flash chromatography on 400 g silica gel, loaded and eluted with 10% ethyl acetate in hexane. Pure fractions were combined and evaporation gave 5.45 g of title ester (84%) as a colorless oil.

C. 3-Phenoxybenzenepropanol

Lithium aluminum hydride solution (20.5 mL, 1M in THF, 20.5 mmol) was added dropwise to a solution of Part B ester (5.45 g, 20.5 mmol) in THF (50 mL) at 0° C. under argon. Stirring was continued for 10 min. Ethyl acetate (5 mL) was added until bubbling ceased. Ethyl ether (300 mL) was added and the organic layer was washed with in HCl solution (2×150 mL), H$_2$O (150 mL), saturated sodium bicarbonate (150 mL), and brine (150 mL), then dried over MgSO$_4$. Evaporation gave a pale yellow oil. Purification was performed by flash chromatography on 500 g silica gel, loaded and eluted with 15% ethyl acetate in hexane. Pure fractions were combined and evaporated to give 4.2 g of title alcohol (90%) as a colorless oil.

D. 1-(3-Iodopropyl)-3-phenoxybenzene

Iodine (1.80 g, 7.24 mmol) in THF (5 mL) was added Go a mixture of Part C. alcohol (1.5 g, 6.58 mmol), triphenylphosphine (1.90 g, 7.24 mmol) and imidazole (0.89 g, 13.2 mmol) in THF (15 mL). The reaction mixture was stirred at RT for 20 min, then diluted with hexane (200 ml). The organic layer was washed with 10% sodium bisulfite (50 mL), saturated sodium bicarbonate (50 mL), brine (50 mL) and dried over MgSO$_4$. The solvent was evaporated to 100 ml volume, 10 g silica gel was added and the mixture was evaporated to dryness. Flash chromatography was performed on 100 g silica gel, loaded and eluted with hexane. Pure fractions were combined and evaporated to give 1.70 g of title iodide (76%) as a colorless oil.

E.

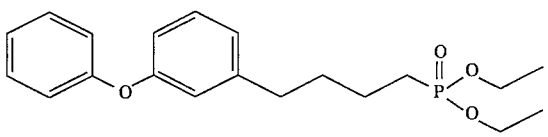

To a stirred solution of 2.88 g (18.6 mmol) of diethyl methylphosphonate in 20 mL of tetrahydrofuran (THF) under argon at −78° C. was added dropwise 6.83 mL (17.1 mmol) of a 2.5M solution of n-butyllithium in hexanes. After the reaction was stirred for one hour at −78° C., 5.0 g (15.5 mmol) of Part D iodide in 20 mL of THF was added and the solution was allowed to warm to room temperature over 2 hours. The clear bright yellow solution was quenched with saturated ammonium chloride and diluted with ether. The organic layer was washed with water and brine, dried (sodium sulfate), and concentrated to provide 5.11 g of a yellow oil, which was purified by flash chromatography on silica gel (250 g) packed and eluted with ethyl acetate. Fractions containing clean product were combined and concentrated to provide 4.57 g (62%) of title compound as a clear oil.

TLC Silica gel (ethyl acetate) $R_f$=0.23.

MS (CI,+ions) m/z 363 (M+H).

IR (CH$_2$Cl$_2$ film) 2982, 2936, 2866, 1584, 1487, 1445, 1250, 1215, 1057, 1024, 959, 785, 694 cm$^{-1}$.

$^1$H NMR (CDCl$_3$,) and $^{13}$C NMR (CDCl$_3$) spectra are consistent with desired product.

F.

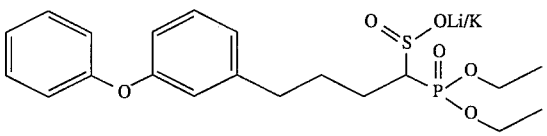

To a stirred solution of 3 mL of THF and 464 mg (1.28 mmol) of Part E compound, which had been evaporated twice from toluene, at −78° C. under argon was treated dropwise with 563 μL (1.41 mmol) of a 2.5 M solution of n-butyllithium in hexanes. A stream of sulfur dioxide was condensed into a separate flask containing 10 mL of THF at −78° C. until the total volume of the solution exceeded 15 mL. The solution of the anion was then added via cannula. The mixture was allowed to warm to room temperature over 16 hours. Excess sulfur dioxide and solvent were removed under a stream of nitrogen and the residue was redissolved in methylene chloride and concentrated to afford 667 mg of a thick yellow oil. The crude product was purified by MPLC on a column of CHP-20P gel (2.5 cm diameter×21 cm height), eluting with water (100 mL), followed by a gradient formed by the gradual addition of 500 mL of acetonitrile to a reservoir of 450 mL of water. Approximately 10 mL fractions were collected. Pure fractions were combined and concentrated to give 413 mg (75%) of title compound, a mixed potassium and lithium salt, as a clear oil.

MS (CI,+ions) m/z 503 (M−Li+2K) 471 (M+K), 465 (M−Li+H+K), 433 (M+H), where M is the lithium salt.

$^1$H NMR (CD$_3$OD) and $^{13}$C NMR (CDCl$_3$) spectra are consistent with desired product.

$^{31}$P NMR (CDCl$_3$, 121 MHz) δ28.0 ppm.

G. 3-Phenoxy-α-phosphonobenzenebutane-sulfinic acid, tripotassium salt

A stirred solution of 391 mg (0.90 mmol) of Part F' compound, which had been evaporated twice from toluene, in 2 mL of methylene chloride was treated sequentially with 0.95 mL (4.52 mmol) of hexamethyl disilazane anc 0.72 mL (5.43 mmol) of trimethylsilyl bromide. The reaction was stirred at room temperature under argon for 24 hours, at which point the organics were removed under vacuum and the residue was dissolved in 2.71 mL of (2.71 mmol) of 1 N KOH and lyophiphized. The solid was purified by MPLC on a column of CHP-20P gel (2.5 cm diameter×21 cm height), eluting with water (100 mL), followed by a gradient formed by the gradual addition of 500 mL of acetonitrile to a reservoir of 450 mL of water. Approximately 10 mL fractions were collected. Pure fractions were combined and concentrated to provide 112 mg (25%) of a white lyophilate. The clean product was combined with 250 mg from another batch (derived from 957 mg (2.64 mmol) of part E compound) and passed through 10 g of AG50W-X8 gel which had been preequilibrated to the potassium form. The fractions containing product were concentrated to provide 225 mg of title compound as a white lyophilate.

TLC Silica gel (6:3:1 n-propanol/ammonia/water) $R_f$=0.12.

MS (FAB,+ions) m/z 523 (M+K) 485 (M+H), 447 (M+2H−K), 409 (M−2K+3H).

IR (KBr) 2959, 2926, 1458, 1385, 1194, 1059 cm$^{-1}$.

$^1$H NMR (D$_2$O)

δ7.31 (t, 1H, J=7 Hz)

7.21 (t, 1H, J=7 Hz)

7.13 (t, 1H, J=7 Hz)

6.99 (d, 1H, J=8 Hz)

6.94 (d, 1H, J=8 Hz)

6.85 (s, 1H)

6.75 (dd, 1H, J=8 and 2 Hz)

2.51 (t, 2H, J=7 Hz)

2.18 (dt, 1H, J=17 and 5 Hz)

1.79 (m, 2H)

1.60 (m, 2H) ppm.

$^{13}$C NMR (D$_2$O)

δ156.9

156.6

145.9

130.1

129.9

123.9

123.8

119.0

118.7

115.9

69.2 (d, J=122 Hz)

35.7

31.6 (d, J=5 Hz)

21.5 ppm.

Analysis Calcd. for C$_{16}$H$_{16}$O$_6$PSK$_3$+4.2 H$_2$O C, 34.26; H, 4.40; P, 5.52; S, 5.72 Found: C, 33.96; H, 4.07; P, 5.14; S, 5.43.

EXAMPLE II

3-Phenoxy-α-phosphonobenzenebutanesulfinic acid, tripotassium salt

To a stirred solution of 186 mg (0.46 mmol) of Example I Part F compound in 0.5 mL of methylene chloride was added 0.422 mL (2.0 mmol) of hexamethyldisilazane followed by 0.634 mL (4.8 mmol) of trimethylsilyl bromide.

The reaction was stopped and stirred at room temperature under argon. After 25 hours, the entire reaction mixture was concentrated under vacuum, then re-treated with 0.5 mL of methylene chloride, 0.88 mL (5.53 mmol) of allyl trimethyisilane, and 0.73 mL (5.53 mmol) of trimethylsilyl bromide. After 10 hours, the reaction was treated with a further 0.37 mL of trimethylsilyl bromide. After a further 12 hours, the reaction mixture was concentrated in vacuo and treated with 1.2 mL of 1N KOH, and applied onto a 15×100 mm column of CHP-20P gel. The column was eluted under medium pressure with 40 mL of water followed by 25 mL each of the following mixtures: 23:2, 21:4, 19:6, 17:8, 15:10, 13:12, and 11:14 water:acetonitrile. The product containing fractions were pooled and concentrated in vacuo to give 116 mg. This material was dissolved in a minimal amount of water and passed through a column of 12 g of AG50W-X8 (100–200 mesh) ion exchange resin that had been equilibrated to potassium form. Product containing fractions were pooled and lyophillized to afford 103 mg (46% yield) of the title compound.

Anal. Calcd for $C_{16}H_{16}O_6PSK_3 + 1.87\ H_2O$: C, 37.08; H, 3.84; P, 5.98; S, 6.19 Found: C, 37.40; H, 3.65; P, 5.60; S, 5.74.

EXAMPLE III (E,E) -6,10,14-Trimethyl-1-phosphono-5,9,13-pentadecatriene-1-sulfinic acid, tripotassium salt

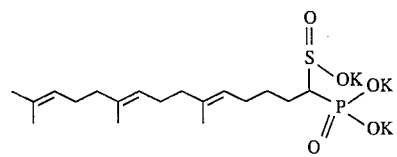

A.

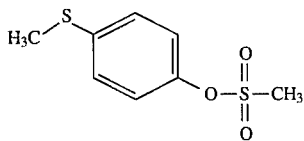

To a solution of 25 g (0.18 mol, 1 eq) of 4-(methylmercapto)phenol in 500 mL of ether at –10° C. was added 37 mL (0.27 mol, 1.5 eq) of triethylamine. After 5 min, a solution of 16.5 mL (0.21 mol, 1.2 eq) of methanesulfonyl chloride in 50 mL of ether was added dropwise over 2 h. The resulting cloudy yellow solution was warmed to room temperature and stirred for 5 h. The reaction was partitioned between ether (100 mL) and water (250 mL) and the resulting organic layer was washed with cold 1N hydrochloric acid, saturated sodium bicarbonate, brine, dried (MgSO₄) and concentrated to afford 41.4 g of a yellow-white solid. Recrystallization from hexanes/chloroform afforded 36.1 g (92%) of the title compound as a white crystalline solid; mp 73°–74° C.

¹H and ¹³C NMR were consistent with the desired product.

TLC Silica gel (25% ethyl acetate in hexanes): $R_f$ 0.24.

B.

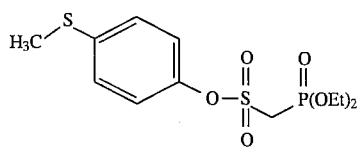

To a solution of 160 mL (160 mmol, 1 eq) of potassium bis(mrimethylsilyl)amide (20% by weight in tetrahydrofuran (THF) from Callery Chem.) at –90° C. (internal temperature) was added a solution of 35 g (160 mmol, 1 eq) of Part A compound in 110 mL of dry THF at a rate to keep the internal temperature below –85° C. (addition took 45 min). The reaction was stirred for 5 min at –90° C., then 13 mL (89 mmol, 0.56 eq) of freshly distilled diethylchlorophosphate was added dropwise at a rate that kept the temperature below –72° C. (addition took 10 min). After stirring at –65° C. for 45 min, the reaction was quenched at –65° C. by the addition of a solution of 9.2 mL (160 mmol, 1 eq) of acetic acid in 10 mL of THF over 5 min. The resulting solution was warmed to room temperature and the majority of the solvent was removed in vacuo. The residue was partitioned between dichloromethane (500 mL) and water (200 mL). The aqueous layer was extracted with dichloromethane and the combined organic layers were dried (MgSO₄) and concentrated to afford 45.5 g of a yellow solid. Flash chromatography on silica gel (800 g) packed and eluted with 35% hexanes in ethyl acetate afforded 16.7 g (53%) of title compound as a pale yellow oil.

¹H and ¹³C NMR, IR and MS were consistent with the desired product.

TLC Silica gel (10% ether in dichloromethane): $R_f$ 0.29.

C.

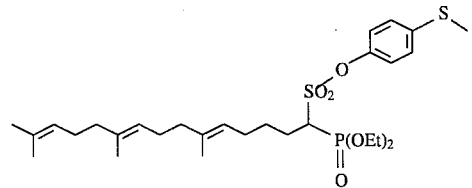

To a suspension of 777 mg (19.4 mmol, 2 eq) of sodium hydride (60% mineral oil dispersion) in 4 mL of dry dimethylformamide (DMF) at 0° C. was added a solution of 7.08 g (20.0 mmol, 1.44 eq) of Part B compound in 8 mL of dry DMF. The heterogeneous bubbling solution was warmed to room temperature and stirred for 30 min. To the resulting homogeneous yellow solution was added 5.0 g (13.9 mmol, 1 eq) of neat iodide

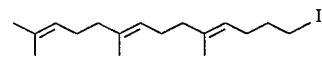

over 2 min and the reaction was stirred for 39 h at room temperature. The reaction was diluted with water and extracted with ether (5×). The combined organic layers were washed with brine, dried (MgSO₄) and concentrated to afford 9.83 g of a yellow oil. Flash chromatography on silica gel (700 g) eluting with 35% ethyl acetate in hexanes afforded 6.48 g (80%) of title compound as a clear light yellow oil.

¹H and ¹³C NMR, IR and MS were consistent with the desired product.

TLC Silica gel (10% ether in hexanes): $R_f$ 0.54.

MS (CI,+ions) M/Z 587 (M+H)

D.

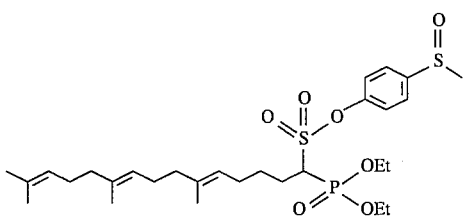

To a solution of 1.0 g (1.7 mmol, 1 eq) of Part C. compound in 20 mL of EtOH at 0° C. was added 1.43 g (17 mmol, 10 eq) of NaHCO₃. To this heterogeneous mixture was added a solution of 1.1 g (1.8 mmol, 1.05 eq) of Oxone® in 6 mL of water in 500 μ portions over 1.5 h. The reaction was diluted with water and extracted with CH₂Cl₂ (5×). The organic solution was dried (Na₂SO₄) and concentrated to afford 995 mg of a clear oil. Flash chromatography on silica gel (75 g) packed and eluted with 2% MeOH in CH₂Cl₂ afforded 747 mg (73%) of title compound as a clear oil.

MS (CI,+ions) M/Z 603 (M+H)

$^1$H and $^{13}$C NMR and IR were consistent with the desired product.

TLC Silica gel (5% MeOH in CH₂Cl₂): $R_f$ 0.29.

E.

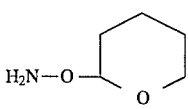

The above compound (H₂NTHP) was prepared as described by Warrener et al, "Synthesis of 1-Hydroxy-2-thiouracil), Angew. Chem. Internat. Edit./Vol. 5 (1966) No. 5, p. 511.

F.

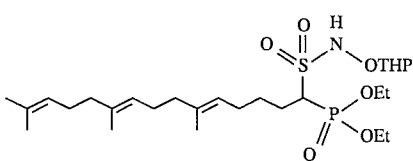

To a solution of 450 mg (0.75 mmol, 1 eq) of Part D compound in 3 mL of toluene was added 437 mg (3.73 mmol, 5 eq) of Part E compound and the resulting solution was stirred at 75° C. for 22 h. The reaction was diluted with ether, washed with 5% KHSO₄, brine, dried (MgSO₄) and concentrated to afford 408 mg of a cloudy oil. Flash chromatography on silica gel (50 g) packed and eluted with 2% MeOH in CH₂Cl₂ afforded 381 mg (90%) of title compound, a mixture of two diastereomers, as a clear, colorless oil.

MS (CI,+ions) M/Z 564 (M+H)

$^1$H and $^{13}$C NMR and IR were consistent with the desired product.

TLC Silica gel (5% MeOH in CH₂Cl₂): $R_f$ 0.58 and 0.66.

G.

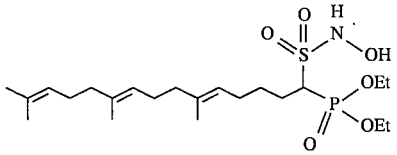

To a solution of 435 mg (0.77 mmol, 1 eq) of Part F compound in 3.5 mL of MeOH at room temperature was added 213 mg (0.85 mol, 1.1 eq) of pyridinium para-toluenesulfonate. The reaction was heated at 40° C. for 90 h. The reaction was cooled and concentrated to afford 730 mg of a yellow oil. Flash chromatography on silica gel (25 g) packed and eluted with 2% MeOH in CH₂Cl₂ afforded 227 mg (61%) of title compound as a clear oil.

$^1$H and $^{13}$C NMR and IR were consistent with the desired product.

MS (CI,+ions) M/Z 497 (M+NH₄)

TLC Silica gel. (5% MeOH in CH₂Cl₂): $R_f$ 0.50.

H. (E,E) -6,10,14-Trimethyl-1-phosphono- 5,9,13-pentadecatriene-1-sulfinic acid, tripotassium salt To a solution of 140 mg (0.29 mmol, 1 eq) of Part G compound in 3 mL of CH₂Cl₂ at room temperature was added 308 μL (1.5 mmol, 5 eq) of hexamethyldisilazane followed by 385 μL (2.9 mmol, 10 eq) of bromotrimethylsilane and the reaction was stirred at room temperature for 40 h. The reaction was concentrated and the residue was dissolved in 1.5 mL (4 eq) of 1M potassium hydroxide followed by 2 mL of water, frozen and lyophilized. The crude lyophilate was purified by MPLC on a column of CHP20P gel (2.5 cm×25 cm) eluting initially with 200 mL of water followed by 500 mL of 15% aqueous acetonitrile. Fractions containing clean product by HPLC were pooled, concentrated, filtered and lyophilized to afford 54 mg (33%) of title compound as a white lyophilate.

TLC silica gel (5: 4: 1 n-propanol:ammonium hydroxide-:water): $R_f$ 0.48.

$^1$H NMR (D₂O):

δ5.17 (t, J=7 Hz)

5.07 (t, J=7 Hz )

5.02 (t, J=7 Hz )

2.12 (dt, J=17 and 6 Hz)

1.93 (m, 10H)

1.79 (m, 2H)

1.54 (s, 3H)

1.50 (s, 3H)

1.47 (s, 6H)

1.43 (m, 2H) ppm.

MS (FAB, +ions): m/z 545 (M+K), 507 (M+H), 469 (M−K+2H).

Anal. Calcd. for C₂₁H₁₉NO₆PSK₃+3.0 H₂O: C, 38.48; H, 6.64; S, 5.71 Found:, C, 38.28; H, 6.61; S, 5.62.

Examples 1 to 177

Examples 1 to 177 compounds of the invention set out above may be prepared following the procedures described herein and in Examples I and II.

What is claimed is:

1. A method for preparing a compound having the structure

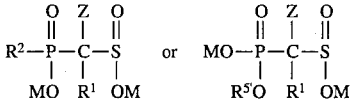

wherein Z is H, halogen, lower allyl or lower alkenyl, $R^1$ is a lipophilic group containing at least 7 carbons, $R^2$ is $R^{5a}$ where $R^{5a}$ is alkyl, arylalkyl or aryl, M is H, a metal ion or other pharmaceutically acceptable cation and $R^{5'}$ is alkyl, arylalkyl, aryl or cycloalkyl, which comprises providing a phosphonosulfonate of the structure

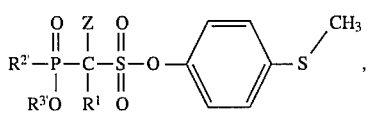

where $R^{2'}$ is $R^{5a}$ or $OR^{5'}$, and $R^{5'}$ is alkyl, arylalkyl, aryl or cycloalkyl, and $R^{3'}$ is alkyl, arylalkyl, aryl or cycloalkyl, reacting the phosphonosulfonate with an oxidizing agent to form the phosphonosulfonate sulfoxide of the structure

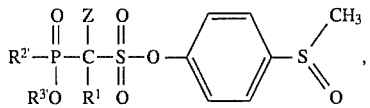

reacting the above phosphonosulfonatesulfoxide with an amine of the structure $NH_2OPG$ where PG represents a protecting group, to form a protected hydroxamic acid of the structure

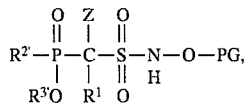

reacting the protected hydroxamic acid with a deprotecting agent to form the hydroxamic acid of the structure

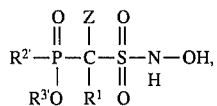

and treating the hydroxamic acid with a silyl bromide or iodide and then with water and/or a base to form the compound of the structure

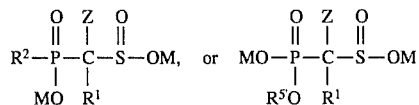

2. A method for preparing a phosphonosulfinate having the structure

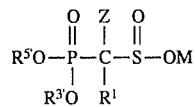

wherein Z is H, halogen, lower alkyl or lower alkenyl, $R^1$ is a lipophilic group containing at least 7 carbons, $R^{5'}$ is alkyl, aryl, arylalkyl, or cycloalkyl, and $R^{3'}$ is alkyl, arylalkyl, aryl or cycloalkyl, and M is H, a metal ion or other pharmaceutically acceptable cation, which comprises providing a compound of the structure

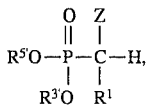

treating the above compound with a base and a sulfinating agent to form the phosphonosulfinate.

3. A method for preparing a phosphonosulfinate having the structure

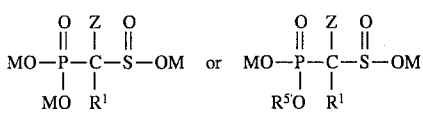

wherein Z is H, halogen, lower alkyl or lower alkenyl, $R^1$ is a lipophilic group containing at least 7 carbons, $R^{5'}$ is alkyl, aryl, arylalkyl or cycloalkyl, M is H, a metal ion or other pharmaceutical acceptable cation, which comprises providing a compound of the structure

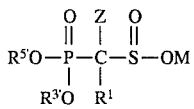

wherein $R^{5'}$ is alkyl, aryl, arylalkyl or cycloalkyl, $R^{3'}$ is alkyl, arylalkyl, aryl or cycloalkyl, and M is H, a metal ion or other pharmaceutically acceptable cation, and treating the phosphonosulfinate with a silyl bromide or silyl iodide followed by water and/or a strong base to form the phosphonosulfinate.

4. The method as defined in claim 1 wherein the oxidizing agent is potassium peroxymonosulfate.

5. The method as defined in claim 1 wherein the protecting group PG is O-tetrahydropyran-2-yl-hydroxylamine or O-tert-butyldimethyl-silylhydroxylamine.

6. The method as defined in claim 1 wherein the protecting group PG is removed with a deprotecting agent which is pyridinium para-toluenesulfonate, p-toluenesulfonic acid or acetic acid.

7. The method as defined in claim 1 wherein the hydroxamic acid is treated with bromotrimethyl silane or iodotrimethyl silane.

8. The method as defined in claim 2 wherein the sulfinating agent is sulfur dioxide.

9. The method as defined in claim 5 wherein the phosphonosulfinate is treated with $(CH_3)_3S_iBr$ or $(CH_3)_3S_iI$.

* * * * *